(12) United States Patent
He et al.

(10) Patent No.: US 12,426,963 B2
(45) Date of Patent: Sep. 30, 2025

(54) TRANSMISSION, DRIVING, AND STERILE ASSEMBLIES, SURGICAL INSTRUMENT AND SYSTEM, AND SURGICAL ROBOT

(71) Applicant: SHANGHAI MICROPORT MEDBOT (GROUP) CO., LTD., Shanghai (CN)

(72) Inventors: Yuyuan He, Shanghai (CN); Sen Yue, Shanghai (CN); Chao He, Shanghai (CN)

(73) Assignee: SHANGHAI MICROPORT MEDBOT (GROUP) CO., LTD., Shanghai (CN)

( * ) Notice: Subject to any disclaimer, the term of this patent is extended or adjusted under 35 U.S.C. 154(b) by 730 days.

(21) Appl. No.: 17/636,733

(22) PCT Filed: Aug. 27, 2020

(86) PCT No.: PCT/CN2020/111869
§ 371 (c)(1),
(2) Date: Feb. 18, 2022

(87) PCT Pub. No.: WO2021/037170
PCT Pub. Date: Mar. 4, 2021

(65) Prior Publication Data
US 2022/0287781 A1 Sep. 15, 2022

(30) Foreign Application Priority Data
Aug. 30, 2019 (CN) .......................... 201910816696.8

(51) Int. Cl.
*A61B 34/30* (2016.01)
*F16D 11/14* (2006.01)
(Continued)

(52) U.S. Cl.
CPC .............. *A61B 34/30* (2016.02); *F16D 11/14* (2013.01); *A61B 2017/00398* (2013.01);
(Continued)

(58) Field of Classification Search
CPC .......... A61B 34/30; A61B 2017/00398; A61B 2017/00477; A61B 2017/00876; F16D 11/14; F16D 2011/008
See application file for complete search history.

(56) References Cited

U.S. PATENT DOCUMENTS

2008/0140088 A1 6/2008 Orban, III
2014/0239042 A1* 8/2014 Simms ............... A61B 17/0682
227/176.1
(Continued)

FOREIGN PATENT DOCUMENTS

| CN | 103533908 A | 1/2014 |
|---|---|---|
| CN | 104411266 A | 3/2015 |

(Continued)

OTHER PUBLICATIONS

International Search Report from PCT/CN2020/111869. Retrieved from Espacenet—Original Document, Search Report. (Year: 2020).*

*Primary Examiner* — Lynsey C Eiseman
*Assistant Examiner* — Skylar Lindsey Christianson
(74) *Attorney, Agent, or Firm* — MUNCY, GEISSLER, OLDS & LOWE, P.C.

(57) ABSTRACT

A transmission assembly, a driving assembly, a sterile assembly, a surgical instrument and system, and a surgical robot. By providing guide surfaces on driving discs constituting the transmission assembly, engagement components can be accurately positioned and engaged by means of the guide surfaces, to achieve the rapid and accurate engage-
(Continued)

ment of the surgical instrument system, avoid the occurrence of coupling failures, and improve the safety and effectiveness of the surgical robot.

24 Claims, 10 Drawing Sheets

(51) Int. Cl.
    *A61B 17/00*         (2006.01)
    *F16D 11/00*         (2006.01)

(52) U.S. Cl.
    CPC ............. *A61B 2017/00477* (2013.01); *A61B 2017/00876* (2013.01); *F16D 2011/008* (2013.01)

(56) References Cited

U.S. PATENT DOCUMENTS

| | | |
|---|---|---|
| 2015/0164593 A1 | 6/2015 | Lohmeier et al. |
| 2015/0257744 A1* | 9/2015 | Alden .................... A61B 34/30 74/625 |
| 2018/0116738 A1 | 5/2018 | Bajo et al. |
| 2018/0168762 A1 | 6/2018 | Scheib et al. |
| 2018/0206931 A1 | 7/2018 | Scheib |
| 2019/0247048 A1 | 8/2019 | Gasparovich et al. |

FOREIGN PATENT DOCUMENTS

| | | | | |
|---|---|---|---|---|
| CN | 104706426 A | * | 6/2015 | ............. A61B 17/00 |
| CN | 105434048 A | | 3/2016 | |
| CN | 106102640 A | | 11/2016 | |
| CN | 106102641 A | | 11/2016 | |
| CN | 107028660 A | | 8/2017 | |
| CN | 107374734 A | | 11/2017 | |
| CN | 108472029 A | | 8/2018 | |
| CN | 207870972 U | | 9/2018 | |
| CN | 109009329 A | | 12/2018 | |
| CN | 208259765 U | | 12/2018 | |
| CN | 109219414 A | | 1/2019 | |
| CN | 109706610 A | | 5/2019 | |
| CN | 209285720 U | | 8/2019 | |
| CN | 110464467 A | | 11/2019 | |
| EP | 3305235 A1 | | 4/2018 | |
| EP | 3007638 B1 | | 5/2018 | |
| EP | 3524178 A1 | | 8/2019 | |
| JP | 2016533817 A | | 11/2016 | |
| JP | 6134768 | | 4/2017 | |
| KR | 101569995 B1 | | 11/2015 | |
| RU | 2642947 C2 | | 1/2018 | |
| RU | 2692231 C2 | | 6/2019 | |
| WO | WO2007089603 A3 | | 1/2008 | |
| WO | WO-2013063522 A2 | * | 5/2013 | ............. A61B 34/30 |
| WO | WO2013153448 A2 | | 10/2013 | |
| WO | WO-2015/116282 A1 | | 8/2015 | |
| WO | WO-2016/176170 A1 | | 11/2016 | |
| WO | WO2018189729 A1 | | 10/2018 | |

* cited by examiner

TRANSMISSION, DRIVING, AND STERILE ASSEMBLIES, SURGICAL INSTRUMENT AND SYSTEM, AND SURGICAL ROBOT

TECHNICAL FIELD

The present disclosure relates to the field of surgical instruments, and more particularly to transmission, driving and sterile assemblies, surgical instrument and system, and surgical robot.

BACKGROUND

In recent years, with the increasing application and development of robotics, particularly computing technology, more and more importance has been attached to the role of surgical robots in clinical practice. On one hand, minimally invasive surgical robot can reduce the physical exertion of the surgeon during an operation. On the other hand, it can achieve the purpose of precision surgery, thus offering advantages of minimal trauma, less bleeding, reduced postoperative infection and fast postoperative recovery.

It is often necessary to sterilize surgical instruments used in surgeries. However, since the surgical robot itself includes many components (e.g., motors, sensors, etc.) that are not suitable to be sterilized using conventional methods, it is impossible to sterilize the entire surgical robot. Therefore, sterile plates in combination with sterile bags are usually used to isolate non-sterilizable parts from sterilizable surgical instruments. However, it is often necessary to frequently exchange surgical instruments during surgery. Moreover, every time the surgical instrument is replaced, the surgical instrument and sterile plate need to be disassembled and assembled. Therefore, it is desirable to achieve the transmission connection between the sterile plate and the surgical instrument in a simple and efficient manner.

Chinese Patent Application No. CN106102640A relates to a method for engaging a surgical instrument with a teleoperated actuator, in which connection of transmission interface is accomplished via rotational couplings between the carriage driver in an instrument manipulator and the instrument driver in the surgical instrument. However, such a design is associated with the following drawbacks: (1) Such a structure provides an axial force to the carriage driver via an elastic component so as to make the carriage driver move axially. However, the axial movements of the carriage driver must result in the presence of circumferential clearance with respect to the input drive shaft, which lead to errors in surgical accuracy and is harmful to the precision surgery; (2) The carriage driver is frictionally coupled to the corresponding instrument driver in such a solution. This tends to lead to coupling failures at some special positions of the rotary disc (see paragraph [0006] of CN106102641A); (3) in order to enable the elastic component to exert an axial force on the carriage driver, it is required to provide stationary components, relative sliding components, limiting components, precise sliding chute in the entire apparatus, which increases the structural complexity of the apparatus. Moreover, it is also required to provide a sufficient axial length of the apparatus to ensure stability of the carriage driver, which makes the apparatus rather bulky; (4) in such a solution, various functions of the apparatus can only be achieved through complex control programs.

Chinese Patent Application No. CN103533908A mentions an instrument interface which drives an instrument by means of the frictional transmission using a tapered structure. This design is associated with the following drawbacks: (1) the interface can be engaged with a drive motor at any position of a drive disk, making it impossible to determine an initial position of the instrument terminal and thus making the robot system unable to acquire absolute position information of the instrument terminal, which is harmful for the ensurence of safety during the surgery; (2) the frictional transmission is associated with a risk of slippage. Once the slippage occurs, the accuracy error would be introduced which may be adverse to the surgical operations.

SUMMARY

It is an object of the present disclosure to provide transmission, driving and sterile assemblies, a surgical instrument, a surgical instrument system and a surgical robot, which allows the quick and fast engagement between the surgical instrument and the sterile plate, and enables to avoid the occurrence of coupling failure and to improve the safety of the surgical robot.

To achieve the above object, The present disclosure provides a transmission assembly for a surgical instrument, comprising a first transmission disk and a second transmission disk, wherein:

the first transmission disk has a second end, and the second transmission disk has a third end arranged to face the second end, one of an end face of the second end and an end face of the third end has a first guide surface formed thereon, the other one of the end face of the second end and the end face of the third end is provided with a second engagement component, wherein at least one first engagement component is provided on the first guide surface, and the second engagement component is configured to be engageable with the first engagement component;

the second engagement component is configured to move along the first guide surface until the second engagement component is engaged with the first engagement component to allow a torque transfer between the first transmission disk and the second transmission disk.

Optionally, the first guide surface has at least one peak and at least one valley that are circumferentially distributed along the end face of the end on which the first guide surface is formed, and the first engagement component is provided at the valley of the first guide surface.

Optionally, an axial projection of the first guide surface has a diameter greater than or equal to one tenth of a peak-to-valley axial distance of the first guide surface.

Optionally, the second end of the first transmission disk is further provided with a first locating pin extending axially, and the third end of the second transmission disk is further provided with a first locating hole extending axially, wherein the first locating pin and the first locating hole are configured to cooperate with each other to facilitate a concentric location of the first transmission disk and the second transmission disk.

Optionally, the first engagement component is a recess, and the second engagement component is a protrusion, wherein a first shield wall surrounding the protrusion is provided on the end face where the second engagement component is provided, and the first shield wall is annular and connected with the protrusion;

and wherein an axial projection of the end face where the first guide surface is situated has a diameter smaller than or equal to an inner diameter of the first shield wall.

Optionally, the second engagement component comprises a first guide portion and a first driving force transmission portion;
  the first guide portion is configured to contact with the first guide surface to guide the second engagement component to slide along the first guide surface, and,
  the first driving force transmission portion is configured to transmit a driving force when the first engagement component is in engagement with the second engagement component.

Optionally, each of an axial projection of the first engagement component and an axial projection of the first driving force transmission portion has a shape of a kidney ellipsoid, or
  each of the axial projection of the first engagement component and the axial projection of the first driving force transmission portion has a shape of a fan, and a fan formed by the first engagement component has an angle greater than or equal to an angle of a fan formed by the first driving force transmission portion.

Optionally, the second engagement component comprises a first guide portion, and wherein the first guide portion is configured to contact with the first guide surface to guide the second engagement component to slide along the first guide surface and to transmit a driving force when the second engagement component is in engagement with the first engagement component.

Optionally, the first guide portion and the first engagement component are configured in a surface contact to increase a frictional force therebetween.

Optionally, at least two second engagement components are provided, and wherein the first guide surface and the second engagement components are configured such that when an axial external force is applied to the second transmission disk and the first guide surface is in contact with the second engagement components, the second engagement components are subject to unbalanced forces.

Optionally, each of the second engagement components comprises a first guide portion, each first guide portion comprising two wedge surfaces that form a first intersection line;
  wherein the first guide surface comprises a plurality of guide sub-surfaces that are connected in sequence, and adjacent guide sub-surfaces form a second intersection line at peaks of the first guide surface; and
  wherein the first and second intersection lines are configured such that when the second engagement components are in contact with the first guide surface at the peaks of the first guide surface, an axial projection of a first intersection line at least partially coincides with an axial projection of a corresponding second intersection lines; or,
  the first and second intersection lines are so configured such that, when the second engagement components are in contact with the first guide surface at the peaks of the first guide surface, at least two of axial projections of a plurality of the first intersection lines are collinear and at least two of axial projections of a plurality of the second intersection lines are collinear.

Optionally, each of the second engagement components comprises a first guide portion, each first guide portion comprising two wedge surfaces and one first transition surface between the two wedge surfaces, wherein the first transition surface is cut by a group of flat or curved imaginary cutting surfaces and a group of cut intersection lines are formed between the first transition surface and the group of flat or curved imaginary cutting surfaces, and wherein a first intersection line is defined as a connecting line formed by connecting each of feature points of the group of cut intersection lines;
  the first guide surface comprises a plurality of guide sub-surfaces, adjacent guide sub-surfaces being connected by a second transition surface at the peak of the first guide surface, wherein the second transition surface is cut by a group of flat or curved imaginary cutting surfaces and a group of cut intersection lines are formed between the second transition surface and the group of flat or curved imaginary cutting surfaces, and wherein a second intersection line is defined as a connecting line formed by connecting each of feature points of the group of cut intersection lines; and
  wherein the plurality of first intersection lines and the plurality of second intersection lines are configured such that when the first engagement component is in engagement with the second engagement components, an axial projection of a first intersection line at least partially coincides with an axial projection of a corresponding second intersection line; or
  a plurality of the first intersection lines and a plurality of the second intersection lines are configured such that when the first engagement component is in engagement with the second engagement components, at least two of axial projections of the plurality of the first intersection lines are collinear and at least two of axial projections of the plurality of the second intersection lines are collinear.

Optionally, a first matching surface is formed on the end face where the second engagement component is situated, and the second engagement component is provided on the first matching surface, wherein the first matching surface is configured not to hinder the second engagement component from moving along the first guide surface and getting into engagement with the first engagement component.

Optionally, the first matching surface is configured such that when the second engagement component is in engagement with the first engagement component, the first matching surface at least partially abuts against the first guide surface.

Optionally, the first guide surface has at least one peak and at least one valley that are circumferentially distributed along the end face where the first guide surface is situated, and the first engagement component is provided at the valley of the first guide surface;
  wherein the first matching surface has at least one peak and at least one valley that are circumferentially distributed along a corresponding end face, and the second engagement component is provided at the peak of the first matching surface;
  wherein the peak of the first matching surface is configured in correspondence with the valley of the first guide surface, and the valley of the first matching surface is configured in correspondence with the peak of the first guide surface; and
  the valley of the first matching surface is configured not to hinder an engagement between the first and second engagement components.

Optionally, the valley of the first matching surface is configured such that when the first transmission disk is in engagement with the second transmission disk, the valley of the first matching surface is not in contact with a corresponding peak of the first guide surface at all; or,
  the valley of the first matching surface is not in contact with a corresponding peak of the first guide surface, while a line contact or a surface contact is formed between two side portions of the valley of the first matching surface and two side portions of the corresponding peak of the first guide surface.

Optionally, the first guide surface has at least one peak and at least one valley that are circumferentially distributed along the end face where the first guide surface is situated, and the first engagement component is provided at the valley of the first guide surface;

wherein the peak of the first matching surface is configured in correspondence with the valley of the first guide surface, and the valley of the first matching surface is configured in correspondence with the peak of the first guide surface; and wherein the first matching surface is further provided with a first accommodating groove thereon, the accommodating groove configured for accommodating the peak of the first guide surface.

Optionally, the transmission assembly further comprises a third transmission disk, wherein the first transmission disk, the second transmission disk and the third transmission disk are coupled in sequence;

wherein the second transmission disk further has a fourth end opposing the third end, and the third transmission disk has a fifth end arranged face to face with the fourth end;

wherein one of an end face of the fourth end and an end face of the fifth end has a second guide surface formed thereon, and the other one of the end face of the fourth end and the end face of the fifth end is provided with a fourth engagement component, wherein at least one third engagement component is provided on the second guide surface, and the fourth engagement component is configured to be engageable with the third engagement component, and wherein the fourth engagement component is configured to slide along the second guide surface until the fourth engagement component is engaged with the third engagement component to allow a torque transfer between the second transmission disk and the third transmission disk.

Optionally, the first engagement component is shaped and sized identically to the third engagement component, wherein the second engagement component is shaped and sized identically to the fourth engagement component, and wherein the first guide surface is shaped identically to the second guide surface.

Optionally, the transmission assembly comprises at least two second transmission disks that are mutually engaged, one of which is engaged with the first transmission disk, and another one of which is engaged with the third transmission disk.

Optionally, the fourth engagement component and the second engagement component are alternately arranged along a circumferential direction of the transmission assembly.

To achieve the above object, present disclosure provides a surgical instrument system for a surgical robot, comprising:

a driving force box comprising a first box body and a driving mechanism disposed in the first box body, the first box body provided thereon with at least one output hole;

a surgical instrument comprising an instrument shaft, an instrument terminal and an instrument box, the instrument box comprising a second box body and a transmission module, wherein the transmission module is disposed in the second box body and configured to drive the instrument shaft and/or the instrument terminal to move, the second box body provided thereon with at least one input hole; and the transmission assembly as defined above, the first transmission disk is disposed in the output hole and the second transmission disk is disposed in the input hole, and wherein when the first transmission disk is engaged with the second transmission disk, a driving force provided by the driving mechanism is transferred by the transmission assembly to the transmission module which in turn drives the instrument shaft and/or the instrument terminal to move.

To achieve the above object, present disclosure further provides a surgical instrument system for a surgical robot, comprising:

a driving force box comprising a first box body and a driving mechanism disposed in the first box body, the first box body provided thereon with at least one output hole;

at least one sterile plate, each provided with at least one transmission hole;

a surgical instrument comprising an instrument shaft, an instrument terminal and an instrument box, the instrument box comprising a second box body and a transmission module, wherein the transmission module is disposed in the second box body and configured to drive the instrument shaft and/or the instrument terminal to move, and the second box body is provided thereon with at least one input hole; and the transmission assembly as defined above, wherein:

the driving force box, the sterile plate and the instrument box are arranged in sequence;

the first transmission disk is provided in the output hole and further comprises a first end opposite to the second end, the first end of the first transmission disk coupled to the driving mechanism; wherein the second transmission disk is provided in the transmission hole, and the third transmission disk is provided in the input hole and further comprises a sixth end opposite to the fifth end, the sixth end of the third transmission disk coupled to the transmission module; and when the first transmission disk, the second transmission disk and the third transmission disk are engaged in sequence, a driving force provided by the driving mechanism is transferred by the transmission assembly to the transmission module which in turn drives the instrument shaft and/or the instrument terminal to move.

Optionally, the surgical instrument system further comprises at least one position correction magnet set, wherein the third transmission disk has a zero position, and the position correction magnet set is configured to help the third transmission disk reach the zero position.

Optionally, the position correction magnet set comprises a first magnet and a second magnet, the first magnet disposed on the third transmission disk, the second magnet disposed on the instrument box, the first and second magnets configured to attract each other to help the third transmission disk reach the zero position.

Optionally, the surgical instrument system further comprises at least one anti-dislocation magnet set, wherein the transmission assembly has a worst position and the anti-dislocation magnet set is configured to prevent the transmission assembly from reaching the worst position.

Optionally, the anti-dislocation magnet set comprises a third magnet and a fourth magnet, the third magnet provided on the second transmission disk, the fourth magnet provided on the sterile plate, and wherein the third and the fourth magnets are arranged to repel each other so as to keep the transmission assembly off the worst position under an action of a repulsive force.

Optionally, the surgical instrument system further comprises a circumferential limiter configured to limit a range of rotation of the third transmission disk.

Optionally, the circumferential limiter comprises a limiting protrusion provided on a circumferential side wall of the third transmission disk and a slide groove provided in an inner wall of the input hole, and wherein the limiting protrusion is provided within the slide groove and is moveable along the slide groove.

Optionally, the surgical instrument system further comprises an axial limiter configured to prevent the second transmission disk from dislodging from the sterile plate.

Optionally, the sterile plate comprises a sterile substrate and a sterile cover, the sterile substrate coupled to the driving force box, the sterile substrate provided thereon with a first through hole, the sterile cover provided thereon with a second through hole, the second through hole constituting the transmission hole together with the first through hole, wherein the axial limiter comprises a limiting collar provided on a circumferential side wall of the second transmission disk, and wherein a section of the second through hole close to the first through hole has an inner diameter greater than each of an inner diameter of a section of the second through hole away from the first through hole and an inner diameter of the first through hole, and matches an outer diameter of the limiting collar.

To achieve the above object, present disclosure further provides a surgical robot comprising the surgical instrument system as defined above.

Optionally, the surgical robot further comprises a robotic arm, wherein the driving force box is fixed to a terminal of the robotic arm, and the instrument box is detachably attached to the driving force box.

To achieve the above object, present disclosure further provides a surgical robot comprising the surgical instrument system as defined above.

Optionally, the surgical robot further comprises a robotic arm, wherein the driving force box is fixed to a terminal of the robotic arm, and the sterile plate is detachably provided on the driving force box, the instrument box detachably attached to the sterile plate.

To achieve the above object, present disclosure further provides a driving assembly for a surgical instrument, which comprises:
 a first box body, on which at least one output hole is provided;
 a driving mechanism disposed in the first box body; and
 a first transmission disk configured to engage with a second transmission disk comprising a second engagement component or with a third transmission disk comprising a fourth engagement component, the first transmission disk disposed in the output hole, wherein the first transmission disk has two opposing end parts, one of which is coupled to the driving mechanism, the other one of which has a guide surface formed on an end face thereof, wherein the guide surface is provided thereon with at least one first engagement component, and the guide surface is configured to allow the second engagement component of the second transmission disk or the fourth engagement component of the third transmission disk to move along the guide surface until it comes into engagement with the first engagement component.

Optionally, the guide surface of the first transmission disk has at least one peak and at least one valley that are arranged along a circumferential direction of a corresponding end part, and the first engagement component is provided at the valley of the guide surface.

Optionally, the guide surface of the first transmission disk is provided with at least two first engagement components that are centro-symmetrically arranged on the guide surface.

To achieve the above object, present disclosure further provides a driving assembly for a surgical instrument, which comprises:
 a first box body, on which at least one output hole is provided;
 a driving mechanism disposed in the first box body; and
 a first transmission disk configured to engage with a second transmission disk comprising a first guide surface and a first engagement component or with a third transmission disk comprising a second guide surface and a third engagement component, the first transmission disk disposed within the output hole, wherein the first transmission disk has two opposing end parts, one of which is coupled to the driving mechanism, and the other one of which has at least one second engagement component formed on an end face thereof, the second engagement component configured to move along the first guide surface until it comes into engagement with the first engagement component or to move along the second guide surface until it comes into engagement with the third engagement component.

Optionally, a first matching surface is formed on an end face of the other one of the end parts of the first transmission disk, and wherein the first matching surface has at least one peak and at least one valley that are arranged along a circumferential direction of the end face, and the second engagement component is located at the peak of the first matching surface.

To achieve the above object, present disclosure further provides a sterile assembly comprising:
 at least one sterile plate provided with at least one transmission hole; and
 at least one second transmission disk configured to engage with a first transmission disk and a third transmission disk, the second transmission disk disposed within the transmission hole, wherein the second transmission disk has two opposing end parts, and at least one of the end parts is provided with a guide surface on an end face thereof, wherein the two end parts of the second transmission disk are each provided with at least one engagement component on the corresponding end face, and wherein the guide surface and the engagement components are configured to enable engagement of the second transmission disk with each of the first and third transmission disks.

Optionally, the guide surface of the second transmission disk has at least one peak and at least one valley that are arranged along a circumferential direction of the corresponding end part, and the engagement component(s) provided on the guide surface is located at the valley of the guide surface.

Optionally, the two end parts of the second transmission disk each have a guide surface formed on the corresponding end face, and at least one engagement component is provided on each guide surface, the engagement component being a recess.

Optionally, only one of the end parts of the second transmission disk has a guide surface formed on its end face, and the engagement component provided on the guide surface is a recess, and wherein the engagement component provided on an end face of the other one of the end parts is a protrusion.

Optionally, the sterile assembly further comprises at least one anti-dislocation magnet set,
wherein the transmission assembly has a worst position and the anti-dislocation magnet set is configured to prevent the transmission assembly from reaching the worst position.

Optionally, the sterile assembly comprises at least two sterile plates stacked together, and the transmission holes in the at least two sterile plates are aligned with one another and each provided therein with one transmission disk.

Optionally, the sterile assembly further comprises an axial limiter configured to prevent the transmission disk from dislodging from the transmission hole.

Optionally, the sterile plate comprises a sterile substrate and a sterile cover, the sterile substrate configured to couple the driving force box, the sterile substrate provided thereon with a first through hole, the sterile cover provided thereon with a second through hole, the second through hole constituting the transmission hole together with the first through hole, wherein the axial limiter comprises a limiting collar provided on a circumferential side wall of the second transmission disk, and wherein a section of the second through hole close to the first through hole has an inner diameter greater than each of an inner diameter of a section of the second through hole away from the first through hole and an inner diameter of the first through hole, and matches an outer diameter of the limiting collar.

To achieve the above object, present disclosure further provides a sterile assembly, which comprises:
at least one sterile plate each provided with at least one transmission hole; and
at least one second transmission disk configured to engage with a first transmission disk comprising a first guide surface and a first engagement component and with a third transmission disk comprising a second guide surface and a third engagement component, the second transmission disk disposed in the transmission hole, wherein the second transmission disk has two opposing end parts, each having at least one engagement component formed on an end face thereof, the engagement components configured to enable engagement of the second transmission disk with each of the first and third transmission disks.

Optionally, the two opposing end parts of the second transmission disk each have a matching surface formed on the corresponding end face, and the matching surface is provided with at least one peak and at least one valley that are arranged along a circumferential direction of the corresponding end face, and wherein each of the engagement components is provided at a peak of a corresponding matching surface.

To achieve the above object, present disclosure further provides an instrument box assembly for a surgical instrument comprising an instrument shaft and an instrument terminal, which comprises:
an instrument box comprising a second box body and a transmission module disposed in the second box body, the transmission module configured to drive the instrument shaft and/or the instrument terminal to move, the second box body having at least one input hole provided thereon; and
a third transmission disk configured to engage with a first transmission disk comprising a second engagement component or with a second transmission disk comprising a fourth engagement component, the third transmission disk disposed in the input hole, wherein the third transmission disk has two opposing end parts, one of which is coupled to the transmission module, and the other one of which has a guide surface formed on an end face thereof, wherein the guide surface is provided thereon with at least one third engagement component, and the guide surface is configured to allow the second engagement component of the first transmission disk to move along the guide surface until it comes into engagement with the third engagement component or to allow the fourth engagement component of the second transmission disk to move along the guide surface until it comes into engagement with the third engagement component.

Optionally, the guide surface of the third transmission disk has at least one peak and at least one valley that are arranged along a circumferential direction of a corresponding one of the end parts, and wherein the third engagement component is provided at the valley of the guide surface.

Optionally, the transmission module comprises a rotating member, a flexible member and a group of guide pulleys, the group of guide pulleys configured to alter an extension direction of the flexible member, the rotating member configured to drive the instrument terminal to rotate via the flexible member, wherein the rotating member is detachably coupled to or integrally formed with the third transmission disk.

Optionally, the surgical instrument further comprises at least one position correction magnet set,
the third transmission disk has a zero position, and the position correction magnet set is configured to help the third transmission disk reach the zero position.

Optionally, the surgical instrument further comprises a circumferential limiter configured to restrain a range of rotation of the third transmission disk.

To achieve the above object, present disclosure further provides an instrument box assembly for a surgical instrument comprising an instrument shaft and an instrument terminal, which comprises:
an instrument box comprising a second box body and a transmission module disposed in the second box body, the transmission module configured to drive the instrument shaft and/or the instrument terminal to move, the instrument box having at least one input hole provided thereon; and
a third transmission disk configured to engage with a first transmission disk comprising a first guide surface and a first engagement component or with a second transmission disk comprising a second guide surface and a third engagement component, the third transmission disk disposed in the input hole, wherein the third transmission disk has two opposing end parts, one of which is coupled to the transmission module, and the other one of which has at least one fourth engagement component formed on an end face thereof, the fourth engagement component configured to move along the first guide surface until it comes into engagement with the first engagement component of the first transmission disk or to move along the second guide surface until it comes into engagement with the third engagement component of the second transmission disk.

Optionally, the other one of the two opposing end parts has a first matching surface formed on an end face thereof, the first matching surface having at least one peak and at least one valley that are arranged along a circumferential direction of the corresponding end face, and wherein the fourth engagement component is provided at the peak of the first matching surface.

Compare to the prior art, the transmission, driving and sterile assemblies, the surgical instrument, the surgical instrument system and the surgical robot of present disclosure has the following advantages:

Firstly, the transmission assembly for a surgical instrument includes at least a first transmission disk and a second transmission disk. The first transmission disk has a second end, and the second transmission disk has a third end arranged face to face with the second end. The end face of the second or third end has a first guide surface formed thereon, and at least one first engagement component is provided on the first guide surface. Moreover, the other end face of the second or third end is provided with a second engagement component that is engagable with the first engagement component. The second engagement component is configured to move along the first guide surface until it is engaged with the first engagement component to allow a torque transfer between the first transmission disk and the second transmission disk. The guiding function of the first guide surface and the engagement configuration between the first and second engagement components enable to avoid the occurrence of an engagement failure. Moreover, the combination of the first guide surface and the second engagement component allows to achieve a fast engagement without the arrangement of an additional control programme.

Secondly, the transmission assembly further includes a third transmission disk. The first transmission disk, the second transmission disk and the third transmission disk are coupled in sequence. The second transmission disk further has a fourth end opposing the third end, and the third transmission disk has a fifth end arranged face to face with the fourth end. The end face of the fourth or fifth ends has a second guide surface formed thereon, and at least one third engagement component is provided on the second guide surface. Moreover, the other end face of the fourth or fifth ends is provided with a fourth engagement component that is engagable with the third engagement component. The fourth engagement component is configured to slide along the second guide surface until the fourth engagement component is engaged with the third engagement component to allow a torque transfer between the second transmission disk and the third transmission disk. The guiding function of the second guide surface and the engagement configuration between the third and fourth engagement components enable to equip the surgical instrument system with a sterile plate to isolate the driving assembly from the surgical instrument, so that there is no need to disinfect the whole surgical robot system.

Thirdly, by providing the first and second matching surfaces and arranging the second and fourth engagement components on the first and second matching surfaces respectively, it enables to improve stress conditions between the second and fourth engagement components during the transmission and enhance the structural strength of the transmission disks to prolong their working life.

Fourthly, the first shield wall connected to the second engagement component and arranged on the periphery of the second engagement component allows to not only improve the stress condition of the second engagement component during the transmission but also reduce the axial size of the entire transmission assembly, thereby enabling to increase the axial size utilization rate and further reduce the weight of the transmission assembly. Similarly, the second shield wall connected to the fourth engagement component and arranged on the periphery of the fourth engagement component allows to improve the stress condition of the second engagement component during the transmission, thereby enabling to increase the axial size utilization rate and further reduce the weight of the transmission assembly.

BRIEF DESCRIPTION OF THE DRAWINGS

FIG. 7a is a schematic exploded view of a variant of the transmission assembly of FIG. 5a.

FIG. 7c is a schematic exploded view of another variant of the transmission assembly of FIG. 5a.

FIG. 7e is a schematic exploded view of a further variant of the transmission assembly of FIG. 5a.

FIG. 7g is a schematic exploded view of a further variant of the transmission assembly of FIG. 5a.

FIG. 9b is a schematic exploded view of the transmission assembly of FIG. 9a.

Figure 1:
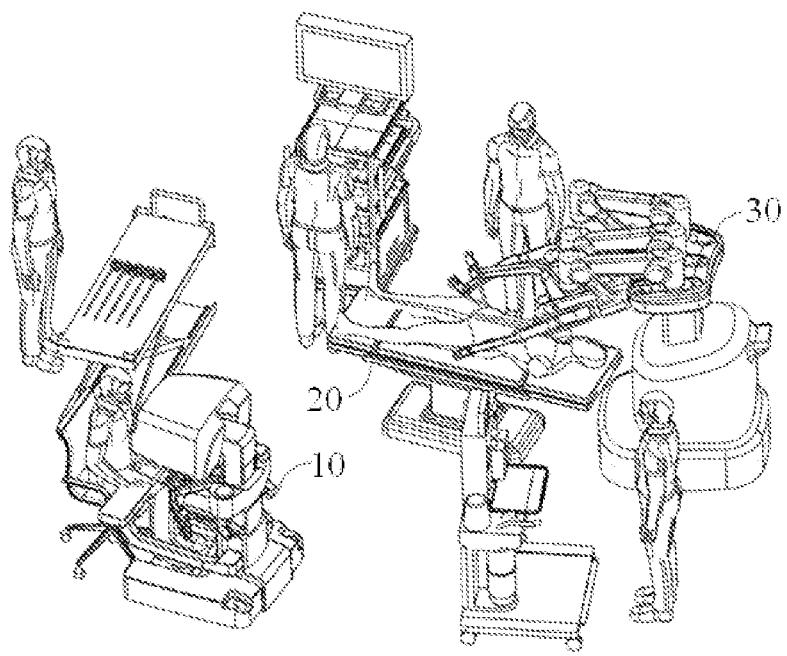
FIG. 1 schematically illustrates a surgical robot in operation according to an embodiment of present disclosure.

In the figures,
10—surgeon console; 20—surgical cart; 30—patient-side cart;
100—driving assembly;
200—sterile assembly;
300—surgical instrument;
310—instrument terminal; 320—instrument shaft;
400—trocar;
1000—transmission assembly;
1100—first transmission disk;
1110—first coupling post; 1120—second coupling hole; 1130—locking hole; 1140—first locating pin;
1200—second transmission disk;
1210—first locating hole; 1220—second locating pin; 1230—limiting collar;
1300—third transmission disk;
1310—second coupling post; 1320—second coupling hole; 1330—second locating hole; 1340—receiving hole; 1350—limiting protrusion;
1010—first guide surface;
1011, 1011'—first guide sub-surfaces;
1020—first engagement component;
1030—second engagement component;
1031—first driving force transmission portion; 1032—first guide portion;
1040—second guide surface;
1050—third engagement component;
1060—fourth engagement component;
1061—second transmission section; 1062—second guide portion;
1001—first matching surface; 1002—first accommodating groove; 1003—second matching surface; 1004—second accommodating groove; 1005—first shield wall; 1006—second shield wall;
2000—driving mechanism;
3000—first box body;
4000—sterile plate; 4000a—first sterile plate; 4000b—second sterile plate;
4100—sterile substrate; 4200—sterile cover;
5000—second box body;
6000—position correction magnet set;
6100—first magnet; 6200—second magnet;
7000—anti-dislocation magnet set;
7100—third magnet; 7200—fourth magnet.

DETAILED DESCRIPTION

In order to make objects, advantages and features of present disclosure more apparent, the transmission assembly, surgical instrument system, surgical robot, driving assembly, sterile assembly and surgical instrument proposed in present disclosure are described below in great detail in conjunction with the drawings. It should be noted that the figures are provided in a very simplified form not necessarily drawn to exact scale for the only purpose of helping to explain embodiments of present disclosure in a more convenient and clearer way.

As used herein and in the appended claims, the singular forms "a", "an" and "the" include plural referents, and the phrase "a plurality of" is used in the sense including "two or more", unless the context clearly dictates otherwise. As used herein and in the appended claims, the term "or" commonly includes the sense of "and/or", unless the context clearly dictates otherwise. Further, the terms "installation", "connection" and "coupling" should be interpreted in a broad sense. For example, a connection may be a fixed, detachable or integral connection, or a mechanical or electrical connection, a direct or indirect connection with one or more intervening elements, or an internal communication or interaction between two individual elements. Those of ordinary skill in the art can understand the specific meanings of the above-mentioned terms herein according to the specific circumstances. Throughout the accompanying drawings, the same or similar reference numerals refer to the same or similar elements.

FIG. 1 schematically illustrates a surgical robot in operation according to an embodiment of present disclosure. As shown in FIG. 1, the surgical robot includes a control station and an effector station. The control station includes a surgeon console 10 provided with master manipulators, while the effector station includes a surgical cart 20, a patient-side cart 30 and other equipment. The patient is lying on the surgical cart 20 for surgery. The patient-side cart 30 is provided with robotic arms (not shown in the Figures) for mounting surgical instrument systems. Each of the robotic arm and surgical instrument system has a predetermined mapping relationship with the master manipulator, so that a master-slave relation is formed therebetween, and each of the robotic arm. Each of the robotic arm and the surgical instrument system move towards various directions following with movements of the master manipulators, so as to complete the surgery operation.

Figures 2A, 2B:
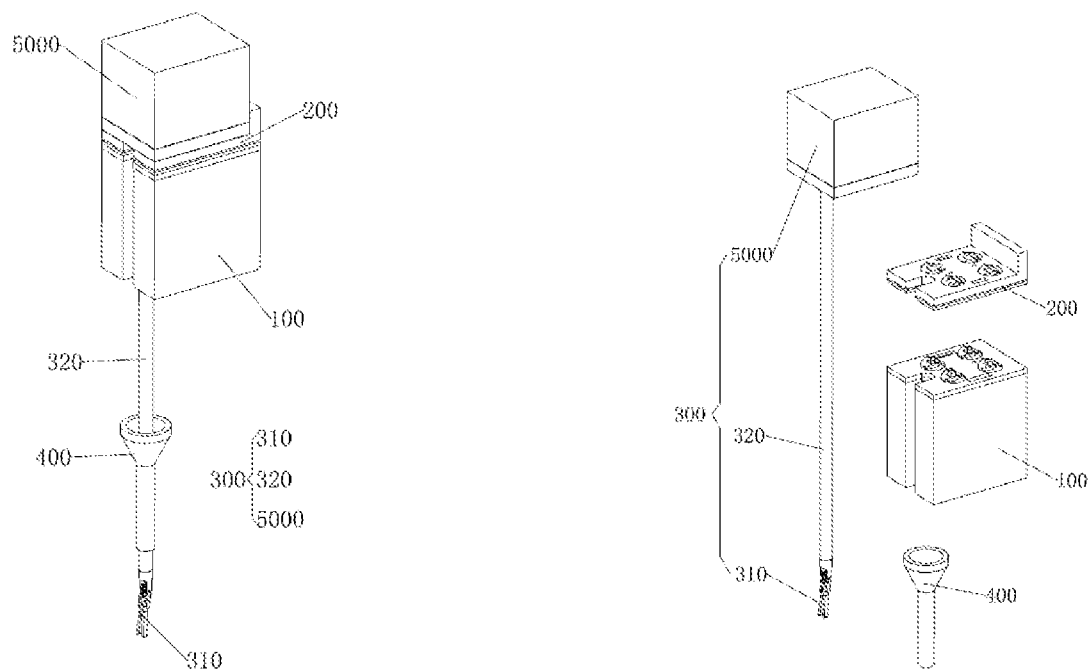
FIG. 2a is a structural schematic of a surgical instrument system according to an embodiment of present disclosure.
FIG. 2b schematically illustrates the surgical instrument system of FIG. 2a that is disassembled.

As shown in FIGS. 2a and 2b, each surgical instrument system includes a driving assembly 100, a sterile assembly 200 and a surgical instrument 300. The surgical instrument 300 includes an instrument box assembly and an instrument terminal 310 coupled to the instrument box assembly. The instrument box assembly is provided thereon with a transmission interface. The driving assembly 100 is configured to drive the surgical instrument 300. The sterile assembly 200 is configured to provide a driving force transmission medium for the transmission interfaces of the driving assembly 100 and the instrument box assembly that are disposed on opposing sides of a sterile bag (e.g., a sterile side and a non-sterile side). The transmission interface arranged in the instrument box assembly receives a torque transferred from the driving assembly 100 and drives various joints of the instrument terminal 310 to move. The surgical instrument 300 further includes an instrument shaft 320. If the instrument shaft 320 is rotatably coupled to the instrument box assembly, the transmission interface arranged in the instrument box assembly receives a torque transferred from the driving assembly 100 and drives the instrument shaft 320 to rotate on its axis.

In general, both the driving assembly 100 and the sterile assembly 200 are provided with transmission interfaces. The transmission interfaces of the driving assembly 100 and the sterile assembly 200 match the transmission interfaces of the instrument box assembly. These transmission interfaces form a transmission assembly by being connected one another to transfer the driving force provided by the driving assembly 100 to the instrument terminal 310, thus causing the instrument terminal 310 to perform various motions. Further, the driving assembly 100 includes a driving force box and transmission disks disposed on the driving force box. The driving force box is fixed to the robotic arm terminal. For example, the robotic arm terminal includes a moveable joint, and the driving force box is disposed on the moveable joint so as to move with movements of the moveable joint. The sterile assembly 200 is arranged on the sterile bag and is detachably coupled to the driving assembly 100. Further, the sterile assembly 200 includes a sterile plate and transmission disks provided on the sterile plate. The sterile plate is detachably disposed on the driving force box. The surgical instrument 300 is detachably coupled to the sterile assembly 200 via the instrument box assembly. Further, the instrument box assembly further includes an instrument box and transmission disks provided on the instrument box, and the instrument box is detachably coupled to the sterile plate. In an alternative embodiment, the surgical robot may be overall sterilized using a special method (e.g., ozone sterilization, hydrogen peroxide sterilization, etc.). In this case, the surgical instrument system may include the driving assembly 100 and the surgical instrument 300. Accordingly, the transmission assembly is constituted by connecting the transmission interfaces of the driving assembly 100 with the corresponding transmission interfaces of the instrument box assembly, so as to transfer the driving force provided by the driving assembly 100 directly to the instrument terminal 310.

The first object of embodiments of present disclosure is to provide a transmission assembly 1000 suitable for use in a surgical instrument system of a surgical robot. As shown in FIGS. 5a to 5g, the transmission assembly 1000 provided in embodiments of present disclosure includes a first transmission disk 1100, a second transmission disk 1200 and a third transmission disk 1300, which are arranged in sequence. The first transmission disk 1100 has a first end and a second end opposite to the first end. The second transmission disk 1200 has a third end and a fourth end opposite to the third end. The third end and the second end are arranged face to face. The third transmission disk 1300 has a fifth end and a sixth end opposite to the fifth end. The fifth end and the fourth end are arranged face to face.

The first guide surface 1010 is provided on one of the end face of the second end and the end face of the third end. The first engagement component 1020 is provided on the first guide surface 1010, and the second engagement component 1030 is provided on the other one of the end face of the second end and the end face of the third end. The second guide surface 1040 is provided on one of the end face of the fourth end and the end face of the fifth end. The third engagement component 1050 is provided on the second guide surface 1040, and the fourth engagement component 1060 is provided on the other one of the end face of the fourth end and the end face of the fifth end.

The second engagement component 1030 is configured to slide along the first guide surface 1010 until it comes into engagement with the first engagement component 1020, so as to achieve the torque transmission between the first and second transmission disks. The fourth engagement component 1060 is configured to slide along the second guide surface 1040 until it comes into engagement with the third engagement component 1050, so as to achieve the torque transmission between the second and third transmission disks.

By configuring the first guide surface 1010 to guide the sliding direction of the second engagement component 1030, the second engagement component 1030 allows to precisely move to the position corresponding to the first engagement component 1020 and get into engagement with the first engagement component 1020, thus allowing to avoid the coupling failure caused by the misalignment between the first transmission disk 1100 and the second transmission disk 1200. Likewise, by configuring the second guide surface 1040 to guide movements of the fourth engagement component 1060, the quick engagement between the fourth engagement component 1060 and the third engagement component 1050 can be achieved, thereby achieving the connection between the second transmission disk 1200 and the third transmission disk 1300.

In practical use, as shown in FIG. 2b, the first transmission disk 1100 is situated in the transmission interface of a driving assembly 100, and the first end of the first transmission disk is coupled to a driving mechanism. The second transmission disk 1200 is situated in a transmission interface of a sterile assembly 200. The third transmission disk 1300 is situated in a transmission interface of an instrument box assembly and is coupled to an instrument terminal 310 via a transmission mechanism. As such, the first transmission disk 1100, the second transmission disk 1200 and the third transmission disk 1300 are engaged one another to make up the transmission assembly 1000 and transfer the driving force provided by the driving mechanism to the instrument terminal 310 to control movements of the instrument terminal 310.

Further, the first engagement component 1020 may be a recess, and the second engagement component 1030 may be a protrusion matching the recess. The third engagement component 1050 may be a recess, and the fourth engagement component 1060 may be a protrusion matching the recess.

Further, the first guide surface has at least one peak and at least one valley that are circumferentially distributed along the end face of the end on which the first guide surface is formed. The second guide surface has at least one peak and at least one valley that are circumferentially distributed along the end face of the end on which the second guide surface is formed. Further, the first engagement component 1020 is provided at the valley of the first guide surface 1010 and the third engagement component 1050 is provided at the valley of the second guide surface 1040. As such, the second engagement component 1030 may be slidable on the first guide surface 1010 along the direction of from the peak to the valley until the second engagement component comes into engagement with the first engagement component 1020. In this process, i.e., the process of sliding from the mutual stagger configuration at the peak of first guide surface to the mutual engagement configuration at the valley of the first guide surface, an axial size of the transmission assembly 1000 gradually decreases. That is, the axial positional change between the peak and valley of the first guide surface 1010 enables to compensate the axial dimensional change of the transmission assembly 1000 due to the engagement of the first engagement component 1020 with the second engagement component 1300. Likewise, the fourth engagement component 1060 is slidable on the second guide surface 1040 along the direction from the peak to the valley until the fourth engagement component comes into engagement with the third engagement component 1050. The axial positional change between the peak and valley of the second guide surface 1040 enables to compensate the axial dimensional change of the transmission assembly 1000 due to the engagement of the third engagement component 1050 with the fourth engagement component 1060.

Further, one or more first engagement components 1020 may be provided on the first guide surface 1010. Preferably, at least two first engagement components 1020 are centro-symmetrically arranged on the corresponding end face. Likewise, one or more third engagement components 1050 may be provided on the second guide surfaces 1040. Preferably, at least two third engagement components 1050 are centro-symmetrically arranged on the corresponding end face.

Additionally, the shape and size of the first guide surface 1010 and the second guide surface 1040 may be identical or not. The numbers of peak(s) and valley(s) on the first guide surface 1010 and the second guide surface 1040 may be identical or not. The number, shape and size of the first engagement components 1020 and the third engagement components 1050 may be identical or not. The second engagement components 1030 may be provided in a number that is compatible with the number of the first engagement components 1020. That is, the number of the second engagement components 1030 may be either the same as that of the first engagement components 1020 or not. In the latter case, the number of the first engagement components 1020 is greater than that of the second engagement components 1030, and the second engagement components 1030 are arranged in the same manner as at least some of the first engagement components 1030. Likewise, fourth engagement components 1060 may be provided in a number that is compatible with the number of the third engagement components 1050. The specific configurations in these aspects may be determined according to practical needs.

The structure of the transmission assembly 1000 will be described in detail below with reference to the accompanying drawings. In the following various embodiments, the first guide surface 1010 is identical to the second guide surface 1040. Accordingly, the number of the first engagement components 1020 is the same as that of the third engagement components 1050, and the first engagement components 1020, the second engagement components 1030, the third engagement components 1050 and the fourth engagement components 1060 are each centro-symmetrically provided on the respective end faces. However, the present disclosure is not limited to these arrangements. Further, for ease of description, a plane perpendicular to the axis of the transmission assembly 1000 is referred to as a "reference plane" below.

Figure 5A:
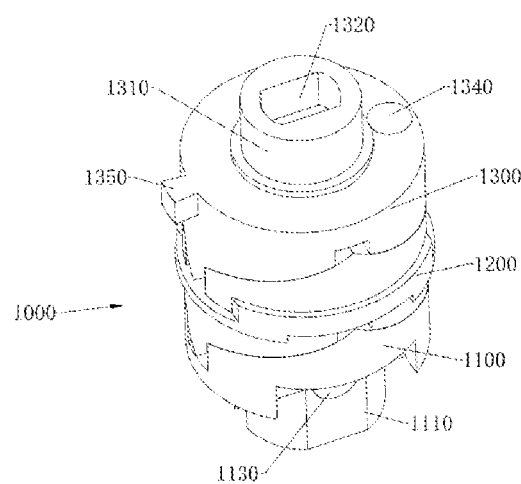
FIG. 5a is a structural schematic of a transmission assembly according to embodiment 1 of present disclosure.
Figure 5B:
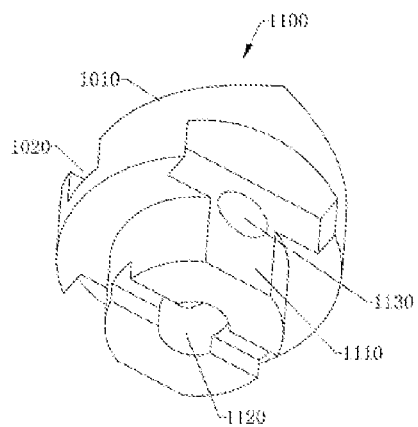
FIG. 5b is a structural schematic of a first transmission disk of the transmission assembly of FIG. 5a taken from one direction.
Figure 5C:
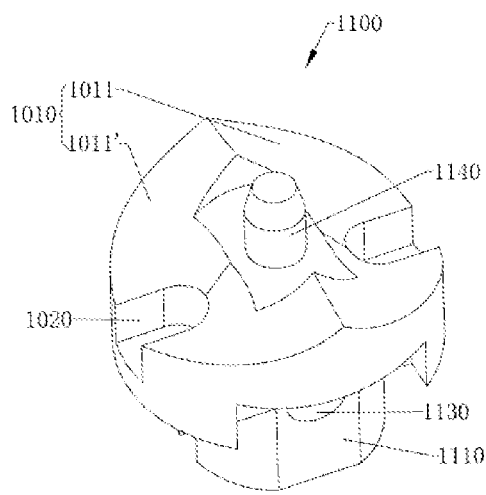
FIG. 5c is a structural schematic of the first transmission disk of FIG. 5b taken from another direction.
Figure 5D:
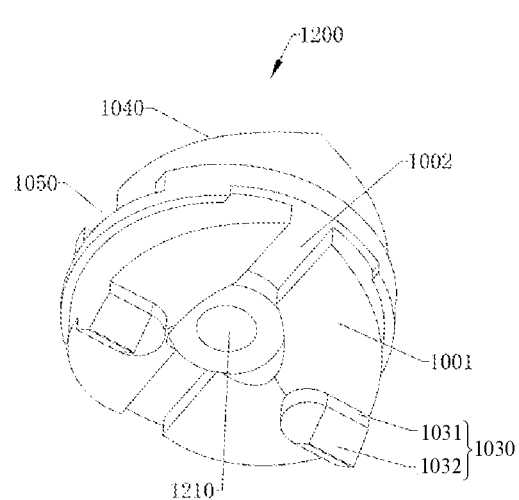
FIG. 5d is a structural schematic of a second transmission disk of the transmission assembly of FIG. 5a taken from one direction.
Figure 5E:
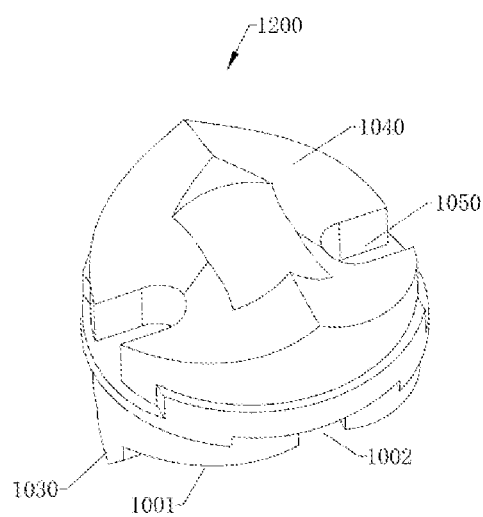
FIG. 5e is a structural schematic of the second transmission disk of FIG. 5d taken from another direction.
Figure 5F:
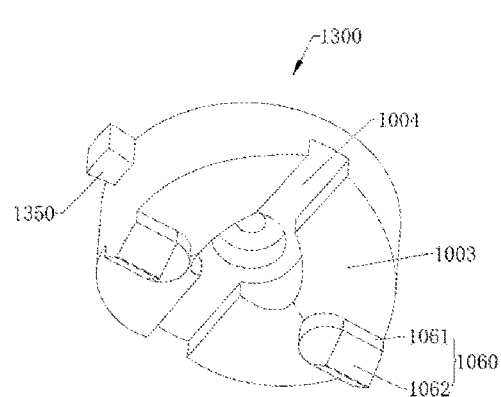
FIG. 5f is a structural schematic of a third transmission disk of the transmission assembly of FIG. 5a taken from one direction.
Figure 5G:
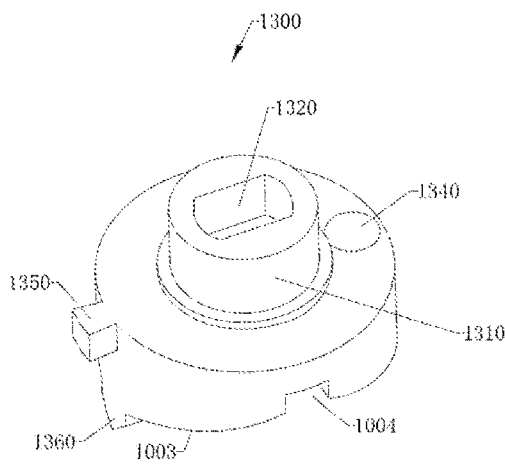
FIG. 5g is a structural schematic of the third transmission disk of FIG. 5f taken from another direction.

Reference is now made to FIGS. 5a to 5g. FIG. 5a is a structural schematic of the transmission assembly 1000 according to embodiment 1. FIGS. 5b and 5c are structural schematics of the first transmission disk 1100. FIGS. 5d and 5e are structural schematics of the second transmission disk 1200. FIGS. 5f and 5g are structural schematics of the third transmission disk 1300. In this embodiment, projections of each of the first transmission disk 1100, the second transmission disk 1200 and the third transmission disk 1300 on the reference plane is circular. That is, the first transmission disk 1100, the second transmission disk 1200 and the third transmission disk 1300 each have a circular circumference. Moreover, the projection of each of the first guide surface 1010 and the second guide surface 1040 on the reference plane is circular. In alternative embodiments, the first transmission disk 1100, the second transmission disk 1200 and the third transmission disk 1300 may assume other shapes such as quincunx. In these cases, for each of the first transmission disk 1100, the second transmission disk 1200 and the third transmission disk 1300, a radius of its projection on the reference plane is defined as the longest center-to-edge distance, while its diameter is defined as twice the radius. Further, regardless of the particular shapes of these disks, the space occupied by rotation of each disk still assume the shape of a revolving body, such as a cylinder, a circular truncated cone or a cone. Therefore, the projection of each of the first transmission disk 1100, the second transmission disk 1200 and the third transmission disk 1300 on the reference plane can be considered as a circle by its center and radius.

As shown in FIG. 5b, in this embodiment, the first end of the first transmission disk 1100 may be coupled to a driving mechanism. Specifically, a first coupling post 1110 may be provided at the first end, and a first coupling hole 1120 configured for receiving an output shaft of the driving mechanism therein may be provided in the first coupling post 1110. Additionally, a locking hole 1130 communicating with the first coupling hole 1120 is provided in a side wall of the first coupling post 1110. The locking hole 1130 is configured to cause the output shaft of the driving mechanism to rotate in synchronization with the first transmission disk 1100. Preferably, an axis of the locking hole 1130 is perpendicular to an axis of the first coupling hole 1120. The driving mechanism, for example the output shaft of the motor, may be inserted in the first coupling hole 1120 and a locking fastener is used to lock the output shaft of the motor at the locking hole 1130.

As shown in FIG. 5c, the end face of the second end of the first transmission disk 1100 has a first guide surface 1010 formed thereon. The first guide surface 1010 has two peaks and two valleys that are arranged along the circumference of the second end. Further, the two peaks are symmetrical with each other with respect to a center of the first guide surface 1010, and the two valleys are also symmetrical with each other with respect to the center of the first guide surface 1010. One first engagement component 1020 is provided at each valley. Preferably, a first locating pin 1140 extending axially is provided at the center of the end face of the second end. The first locating pin 1140 is configured to facilitate the location when the first transmission disk 1100 is engaged with the second transmission disk 1200. Moreover, the circular projection of the first guide surface 1010 on the reference plane has a diameter of d. That is, the axial projection of the first guide surface 1010 has a diameter of d. Further, the first guide surface 1010 has a peak-to-valley axial distance of h, which satisfies $h \geq \frac{1}{10}d$.

Further, a first matching surface 1001 is formed on the end face of the third end, and the second engagement components 1020 is provided on the first matching surface 1001. This embodiment is not limited to any particular shape of the first matching surface 1001, as long as it does not hinder movements of the second engagement components 1030 along the first guide surface 1010 and engagement of the second engagement components 1030 with the first engagement components 1020. In other words, the first matching surface 1001 may either contact the first guide surface 1010 or not. Preferably, when the second engagement components 1030 are into engagement with the first engagement components 1020, the first guide surface 1010 at least partially fits the first matching surface 1001.

Referring to FIG. 5d, two second engagement components 1030 are arranged on the third end of the second transmission disk 1200. Preferably, the two second engagement components 1030 are symmetrical arranged with respect to a center of the end face of the third end. In this embodiment, first matching surface 1001 has two peaks and two valleys that are arranged along the circumference of the third end. One second engagement components 1030 is provided at each of the two peaks. Moreover, a first accommodating groove 1002 for receiving the peak of the first guide surface 1010 may be provided at the valley. The first matching surface 1001 can substantially abut against the first guide surface 1010. Through providing the first matching surface 1001, when the second engagement components 1030 are into engagement with the first engagement components 1020 for transmission, excessive length of the axial cantilever of the second engagement components 1030 can be avoided, thus improving stress conditions of the second engagement components 1030 and extending service life of the second engagement components 1030. Moreover, the first matching surface 1001 also can enhance the structural strength of the second transmission disk 1200.

With continued reference to FIG. 5d, the second engagement component 1030 may include a first driving force transmission portion 1031 and a first guide portion 1032 that are joined together. The end of the first driving force transmission portion 1031 away from the first guide portion 1032 is coupled to the first matching surface 1001, and the first driving force transmission portion 1031 is configured to transfer a torque when it comes into engagement with the first engagement components 1020. This embodiment is not limited to any particular shape of the first driving force transmission portion 1031, as long as it can form a circumference contact (such as, point contact, line contact, or surface contact) when it comes into engagement with the first engagement component 1020. Preferably, a projection of the first driving force transmission portion 1031 on the reference plane has a shape matching with the shape of the projection of the first engagement component on the reference plane. For example, when the projection of the first engagement component 1020 on the reference plane has a shape of a kidney ellipsoid, the projection of the first driving force transmission portion 1031 on the reference plane also has a shape of a kidney ellipsoid. That is, the first engagement component 1020 is a recess with a shape of a kidney ellipsoid. Here, the recess with a shape of a kidney ellipsoid refers to a recess consisted by two lateral planes and one transition surface and having an open end, where the two lateral planes are parallel to each other, and the open end of the recess is arranged at the side away from an axis of the second transmission disk 1200. The first driving force transmission portion 1031 is also consisted by two lateral planes and one transition surface. Alternatively, the projection of the first engagement component 1020 on the reference plane has a shape of a fan. In this case, the fan-shaped recess also has an open end away from the axis of the second transmission disk 1200. The projection of the first driving force transmission portion 1031 on the reference plane is also in the shape of a fan which, however, has an angle slightly smaller than the angle of the fan formed by the first engagement component 1020.

The first guide portion 1032 is configured to contact with the first guide surface 1010 and to be slidable along the first guide surface 1010. Specifically, the first guide portion 1032 may have a wedge-shaped structure and can include two wedge surfaces. The two wedge surfaces meet at an end of the first guide portion 1032 away from the first driving force transmission portion 1031 to form an intersection line that contacts with the first guide surface 1010. In alternative structures, the two wedge surfaces are connected by a curved transition surface at the end away from the first driving force transmission portion 1031. As such, line or surface contact can be formed between the first guide portion 1032 and the first guide surface 1010. Alternatively, the first guide portion 1032 has a vertex at the end away from the first driving force transmission portion 1031, and the point contact is formed between the vertex and the first guide surface 1010. In other words, this embodiment is not limited to any particular form of the first guide portion 1032 as long as that when the second transmission disk 1200 is subjected to an axial external force and the two first guide portions 1032 come into contact with the first guide surface 1010, the two first guide portions 1032 are subject to unbalanced forces and can thus move along the first guide surface 1010 to get into engagement with the first engagement components 1020. Here, the axial external force refers to not only the external force in parallel to the axial direction and directed toward the second transmission disk, but also the external force directed toward the second transmission disk and having a component in parallel to the axial direction. Further, the surface of the wedge structure may be a continuous curved surface.

Further, a first locating hole 1210 is provided at the center of the third end of the second transmission disk 1200. The first locating hole 1210 is configured to fit with the first locating pin 1140 of the first transmission disk 1100 to facilitate the concentric location of the first transmission disk 1100 and the second transmission disk 1200. The fourth end of the second transmission disk 1200 and the fifth end of the third transmission disk 1300 may be structured in the same way, so a detailed description thereof is omitted.

Referring to FIG. 5e, the end face of the fourth end of the second transmission disk 1200 forms the second guide surface 1040, and two peaks and two valleys are arranged on the second guide surface 1040 along the circumference of the fourth end. Moreover, the third engagement components 1050 are provided at valleys of the second guide surface 1040. The two engagement components 1050 are provided at respective valleys. Additionally, the projection of the second guide surface 1040 on the reference plane is a circle having a diameter of d', and the second guide surface 1040 has a peak-to-valley axial distance of h', which satisfies $h' \geq \frac{1}{10}d'$.

With reference to FIG. 5f, the end face of the fifth end of the third transmission disk 1300 is provided with two fourth engagement components 1060. Preferably, the end face of the fifth end forms a second matching surface 1003, and two peaks and two valleys are arranged on the second matching surface 1003 along the circumference of the fifth end. Moreover, one fourth engagement component 1060 is provided at each peak, and a second accommodating groove 1004 for accommodating the peak of the second guide surface 1040 may be provided at each valley. Preferably, when the fourth engagement components 1060 are into engagement with the third engagement components 1050, the second guide surface 1040 at least partially coincides with the second matching surface 1003. Through providing the second matching surface 1003 and configuring the fourth engagement components 1060 at the peaks of the second matching surface 1003, excessive length of the axial cantilever of the fourth engagement components 1060 can be avoided, thus improving stress conditions of the fourth engagement components 1060 and extending service life of the second engagement components 1030 when the fourth engagement components 1060 gets into engagement with the third engagement components 1050 for transmission. Moreover, the third matching surface 1001 also can enhance the structural strength of the third transmission disk 1300.

With continued reference to FIG. 5f, the fourth engagement components 1060 may be similarly structured as the second engagement components 1030. The fourth engagement component 1060 may include a second driving force transmission portion 1061 and a second guide portion 1062 that are joined together. The end of the second driving force transmission portion 1061 away from the second guide portion 1062 is coupled to the second matching surface, and the second driving force transmission portion 1061 is configured to transfer a torque when it comes into engagement with the third engagement components 1050. This embodiment is not limited to any particular shape of the second driving force transmission portion 1061, as long as it can form a circumference contact (such as, point contact, line contact, or surface contact) with the third engagement component 1050 when it comes into engagement with the third engagement component 1050. Preferably, a projection of the second driving force transmission portion 1061 on the reference plane has a shape matching with the shape of the projection of the first engagement component on the reference plane. For example, when the projection of the first engagement component 1020 on the reference plane has a shape of a kidney ellipsoid, the cross-section of the second driving force transmission portion 1061 perpendicular to the axis may also have a shape of a kidney ellipsoid. Alternatively, when the projection of the first engagement component 1020 on the reference plane has a shape of a fan, the cross-section of the second driving force transmission portion 1061 perpendicular to the axis may also have a shape of a fan.

The second guide portion 1062 is configured to contact with the second guide surface 1040 and to be slidable along the second guide surface 1040. Specifically, the second guide portion 1062 may have a wedge-shaped structure and can include two wedge surfaces. The two wedge surfaces meet at an end of the second guide portion 1062 away from the second driving force transmission portion 1061 to form an intersection line that contacts with the second guide surface 1040. In alternative structures, the two wedge surfaces are connected by a curved transition surface at the end away from the second driving force transmission portion 1061. As such, line or surface contact can be formed between the second guide portion 1062 and the second guide surface 1040. Alternatively, the second guide portion 1062 has a vertex at the end away from the second driving force transmission portion 1061, and the point contact is formed between the vertex and the second guide surface 1060. In other words, this embodiment is not limited to any particular form of the second guide portion 1062 as long as that when the third transmission disk 1300 is subjected to an axial external force and the two second guide portions 1062 come into contact with the second guide surface 1040, the two second guide portions 1062 are subject to unbalanced forces and can thus move along the second guide surface 1040 to get into engagement with the third engagement components 1050. Likewise, the surface of the wedge structure may be a continuous curved surface.

In this embodiment, the first engagement components 1020 are identical to the third engagement components 1050. Accordingly, the second engagement components 1030 may be identical to the fourth engagement components 1060. In alternative embodiments, the first engagement components 1020 may differ from the third engagement components 1050. Accordingly, the second engagement components 1030 may also differ from the fourth engagement components 1060.

Referring to FIG. 5g, the sixth end of the third transmission disk 1300 may be coupled to a transmission module of the instrument box assembly to transfer the torque. Specifically, a second coupling post 1310 may be provided on the sixth end, and the second coupling post 1310 may be provided with a second coupling hole 1320. This embodiment is not limited to any particular structure of the transmission module. For example, the transmission module may include a rotating member, a flexible member and a group of guide pulleys. The flexible member is configured to couple the rotating member to a joint of the instrument terminal 410. The group of guide pulleys is configured to alter an extension direction of the flexible member. The rotating member is configured to drive the joint of the instrument terminal 410 to move via the flexible member. The second coupling hole 1320 is configured to be detachably or fixedly coupled to the rotating member transfer a torque to the transmission module.

The exemplary use method of the transmission assembly 1000 according to this embodiment is described as follows: the second end of the first transmission disk 1100 is arranged face-to-face with the third end of the second transmission disk 1200, and the fourth end of the second transmission disk 1200 is arranged face-to-face with the fifth end of the third transmission disk 1300. Subsequently, the second engagement component 1030 slides along the first guide surface 1010 until it slides into the first engagement component 1020 and comes into engagement with the first engagement component 1020, and the fourth engagement component 1060 slides along the second guide surface 1040 until it slides into the third engagement component 1050 and comes into engagement with the third engagement component 1050. When the first end of the first transmission disk 1100 is coupled to a driving mechanism and the driving mechanism drives the first transmission disk 1100 to rotate, the second engagement components 1030 will cooperate with the first engagement components 1020 to transfer a torque, so that the second transmission disk 1200 rotates with the first transmission disk 1100. Moreover, the fourth engagement components 1060 will cooperate with the third engagement components 1050 to transfer a torque, so that the third transmission disk 1300 rotates.

In a further modification, as shown in FIG. 5c, the first guide surfaces 1010 includes first guide sub-surfaces 1011 and second guide sub-surfaces 1011'. The first guide sub-surfaces 1011 and second guide sub-surfaces 1011' meet at peaks, and form two intersection lines. The two intersection lines are projected on the reference plane to obtain the projection lines labeled as the first projection line and the third projection line. As shown in FIG. 5d, the second engagement component 1030 includes first guide portions 1032, each first guide portion 1032 including two wedge surfaces. The two wedge surfaces meet to form an intersection line. The intersection lines are projected on the reference plane to obtain the projection lines labeled as the second projection line and the fourth projection line. Depending on the shapes of the guide surface and the wedge surfaces, the first to fourth projection lines may be straight or S-, C-, L- or otherwise shaped, which is not particularly limited in this embodiment. The first, second, third and fourth projection lines are configured such that, when the second engagement components 1030 contacts with the first guide surface 1010, the first projection line entirely or partially coincides with the second projection line, and the third projection line entirely or partially coincides with the fourth projection line. Alternatively, the first projection line is collinear with the third projection line, and the second projection line is collinear with the fourth projection line. Preferably, the first and third projection lines are collinear, and intersect with the axis of the transmission assembly 1000. The configurations of the first to fourth projection lines enable to achieve that each of the above first guide portions 1032 is subject to an unbalanced force when it contacts with the first guide surface 1010, which can cause the second engagement components 1030 to move along the first guide surface and come into engagement with the first engagement components, thus enabling the transfer of a torque between the first transmission disk and the second transmission disk. Likewise, the second guide surface 1040 has fifth and seventh projection lines, and the second guide portions 1062 have sixth and eighth projections. The fifth to eighth projection lines are configured similarly as the above-described projection lines so that each of the second guide portions 1062 is subject to an unbalanced force when it is in contact with the second guide surface 1040.

Figure 6A:
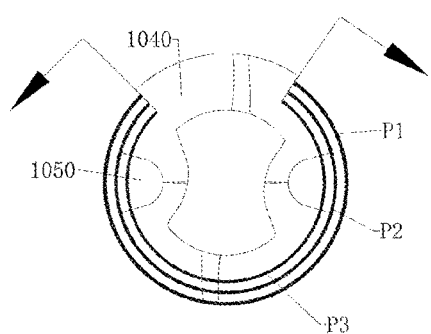
FIGS. 6a and 6b schematically illustrates wedge surfaces of a guide portion connected by a transition surface according to embodiment 1, in which intersection lines are obtained by imaginary cutting surfaces.

In addition, when the guide sub-surfaces are connected by a transition surface, no clear intersection line is existed between the two guide sub-surfaces. Likewise, when the two wedge surfaces of the guide portion are connected by a transition surface, no clear intersection line is existed between the two wedge surfaces. In these cases, the intersection line is defined as follows. The transition surface is cut by a group of flat or curved imaginary cutting surfaces, and a group of cut intersection lines are formed between the transition surface and the group of flat or curved imaginary cutting surfaces. The connecting line formed by connecting each of feature points of the group of cut intersection lines is defined as the intersection line. For example, the feature point is the highest point of the cut intersection line in the axis direction of the transmission disk. As shown in FIG. 6a (the second transmission disc 1200 in FIG. 6a is taken as an example for illustration), the number of the flat or curved imaginary cutting surfaces is at least two. FIG. 6a shows three curved imaginary cutting surfaces P1, P2 and P3, and the highest point refers to the point on the intersection line that are farthest from the center of the second transmission disk 1200 along the axial direction of second transmission disk 1200.

Figure 6B:
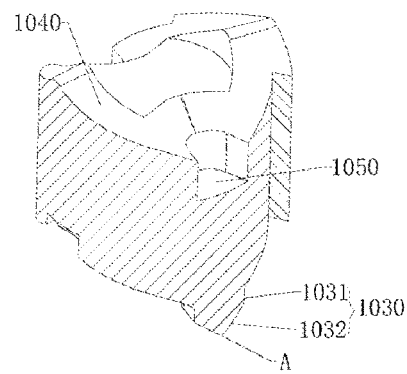

For another example, the flat imaginary cutting surfaces may be arranged in parallel to the axis of the transmission disk, and the group of curved imaginary cutting surfaces may be coaxial cylindrical surfaces. As shown in FIG. 6a, the first guide portion 1032 of the second engagement component 1030 includes two wedge surfaces. The two wedge surfaces are connected by a transition surface. In order to obtain the second and fourth projection lines, the flat imaginary cutting surfaces parallel to the axis of the transmission assembly 1000 may be adopted to cut the first guide portion 1032. As shown in FIG. 6b, the flat imaginary cutting surfaces form cut intersection lines with the first guide portion 1032, and the highest points (i.e., the point A shown in FIG. 6) of the cut intersection lines are taken. When the number of the cutting surfaces is at least two, at least two highest points can be taken. All these highest points are projected to the reference plane to obtain the projection points, and the projection points are connected to obtain the second or fourth projection line. In generally, the more cutting surfaces are used, the higher the accuracy of the obtained second or fourth projection line will be. If the second guide portion 1062 of the fourth engagement components 1060 is configured in a same manner, then the corresponding projection lines are obtained using the same method. Likewise, the second guide surface 1040 is identically configured as the first guide surface 1010, and the fourth engagement components 100 is identically configured as the second engagement components 1030.

Additionally, in this embodiment, the first guide surface 1010 is consisted of a number of curved surfaces, a number of flat surfaces or one continuous curved surface. Similarly, the second guide surface 1040 is consisted of a number of curved surfaces, a number of flat surfaces or one continuous curved surface. The first matching surface 1001 is consisted of a number of curved surfaces, a number of flat surfaces or one continuous curved surface. The second matching surface 1003 is also such configured. In fact, for each of the first transmission disk 1100, the second transmission disk 1200 and the third transmission disk 1300, all intersection surfaces are preferred to smoothly transition from one to another, so as to avoid any sharp junction that may cause damage to the user.

Figure 7A:
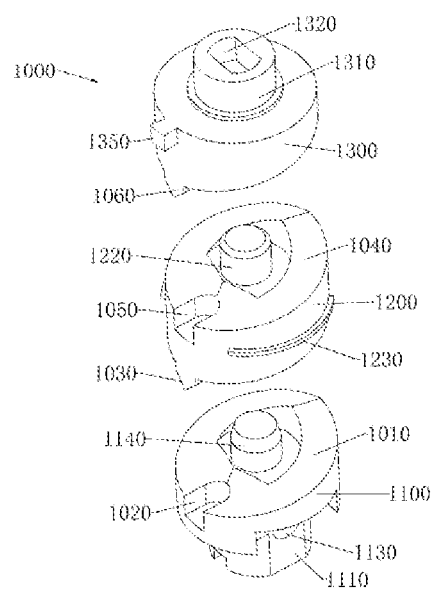
Figure 7B:
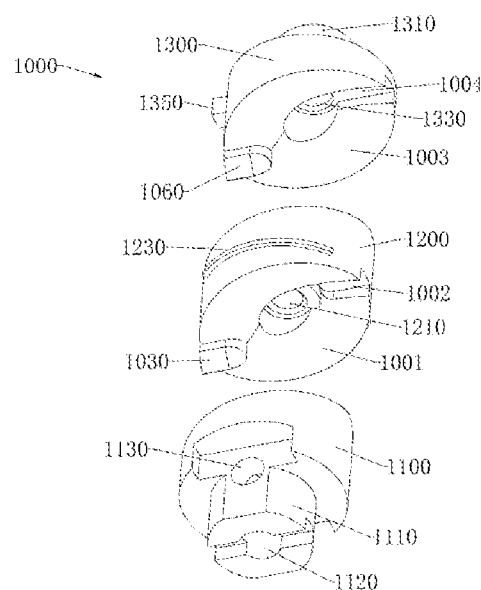
FIG. 7b is a schematic exploded view of the transmission assembly of FIG. 7a taken from another direction.

Reference is now made to FIGS. 7a and 7b which schematically illustrate the structure of a variant of embodiment 1. As shown in FIGS. 7a and 7b, the first guide surface 1010 is formed on the second end of the first transmission disk 1100. The first guide surface 1010 has one peak and one valley that are arranged in a circumferential direction of the second end. Accordingly, one first engagement component 1020 and one second engagement component 1030 are provided. The second guide surface 1040 is formed on the fourth end of the second transmission disk 1200. The second guide surface 1040 has one peak and one valley that are arranged in a circumferential direction of the fourth end. Accordingly, one third engagement component 1050 and one fourth engagement component 1060 are provided. Further, in this embodiment, preferably, the first locating pin 1140 is provided at the center of the second end face of the first transmission disk 1010 and the first locating hole 1210 mating with the first locating pin 1140 is provided at the center of the third end face of the second transmission disk 1200. A second locating pin 1220 is provided at the center of the fourth end face of the second transmission disk 1200, and a second locating hole 1330 mating with the second locating pin 1220 is provided at the center of the fifth end face of the third transmission disk 1300. Through the mating of the first locating pin 1140 and first locating hole 1210 and the mating of the second locating pin 1220 and the second locating hole 1330, it enables to ensure the safety of the transmission process when only one first engagement component 1020, one second engagement component 1030, one third engagement component 1050 and one fourth engagement component 1060 are configured.

In fact, the numbers of the peak(s) and valley(s) on the first guide surface 1010 is determined depending on the number of the first engagement component(s) 1020, while the number of the first engagement component(s) is arranged depending on the required fault-tolerant angle. In general, the greater fault-tolerant angle requires a smaller number of the first engagement components.

For example, when the fault-tolerant angle is 180°, at least two first engagement components 1020 are needed. The "fault-tolerant angle" will be explained in detail below. Besides, thickness (the dimension in the direction of torque transmission) of the first engagement component 1020 relates to the magnitude of the torque. A larger torque requires a greater thickness of the first engagement component 1020. The principle for configuring the first guide surface 1010 also applies to the second guide surface 1040. Besides, for the case that are provided with two or more first engagement components 1020, two or more second engagement components 1030, two or more third engagement components 1050 and two or more fourth engagement components 1060, the first locating pin 1140 and second locating pin 1220 may be provided depending on circumstances.

Figure 7C:
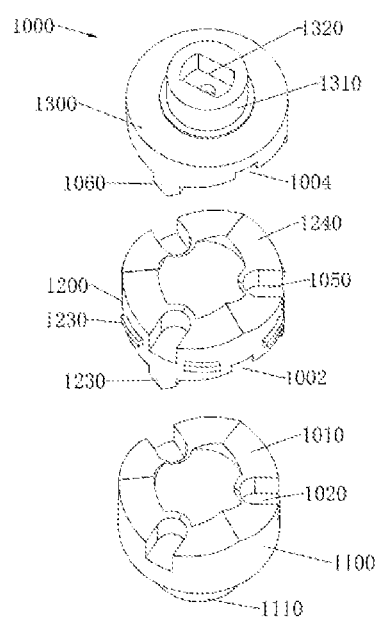
Figure 7D:
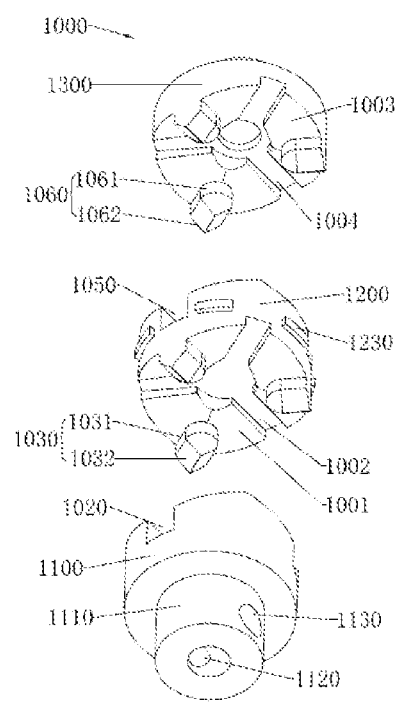
FIG. 7d is a schematic exploded view of the transmission assembly of FIG. 7c taken from another direction.

Reference is now made to FIGS. 7c and 7d, which schematically illustrate the structure of another variant of embodiment 1. As shown in FIGS. 7c and 7d, the first guide surface 1010 is formed on the second end of the first transmission disk 1100, and three peaks and three valleys are provided on the first guide surface 1010. Moreover, the first guide surface 1010 is annular and partially covers part of the second end of the first transmission disk 1100. Three first engagement components 1020 and three second engagement components 1030 are provided.

Figure 7E:
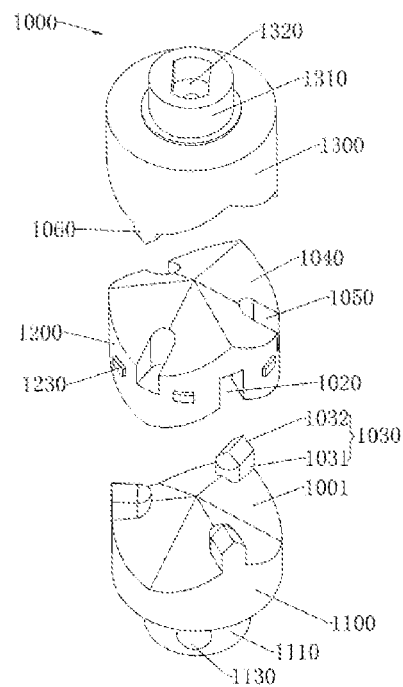
Figure 7F:
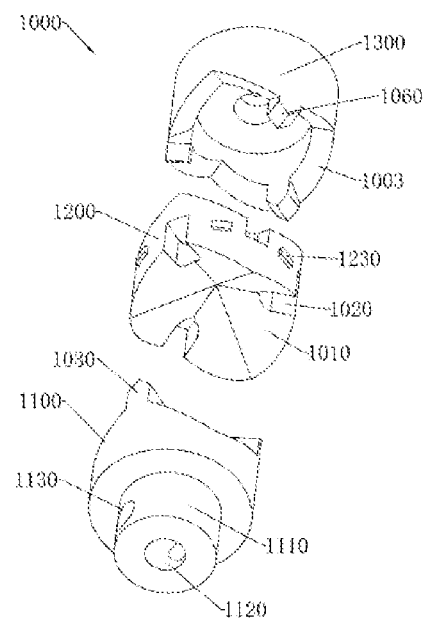
FIG. 7f is a schematic exploded view of the transmission assembly of FIG. 7e taken from another direction.

Reference is now made to FIGS. 7e and 7f, which schematically illustrate the structure of a further variant of embodiment 1. As shown in FIGS. 7e and 7f, the first matching surface 1001 is provided on the second end of the first transmission disk 1100. The first guide surface 1010 is formed at the third end of the second transmission disk 1200, and the second guide surface 1040 is formed at the fourth end of the second transmission disk 1200, the second matching surface 1003 provided at the fifth end of the third transmission disk 1300. Moreover, the second matching surface 1003 is an annular surface and partially covers the fifth end of the third transmission disk 1300. The second matching surfaces 1003 has three peaks and three valleys. Accordingly, three fourth engagement components 1060 and three third engagement components 1050 are provided. There is no first accommodating groove provided on the first matching surface 1001. This embodiment is not limited to any particular shape of the valley of the first matching surface 1001, as long as the valley of the first matching surface 1001 not hinder engagement of the first transmission disk 1100 with the second transmission disk 1200. That is, when the peaks of the first guide surface 1010 fit with the valleys of the first matching surface 1001, the first transmission disk 1100 comes into engagement with the second transmission disk 1200. In other words, the shape of the valley on the first matching surface 1001 is configured such that, when the first transmission disk 1100 is into engagement with the second transmission disk 1200, there is no contact between the valleys of the first matching surface 1001 and the peaks of the first guide surface 1010 (e.g., the first matching surface 1001 is not in contact with the first guide surface 1010 at all; or the valley of the first matching surface 1001 is not in contact with a corresponding peak of the first guide surface 1010, while a line contact or a surface contact is formed between two side portions of the valley of the first matching surface 1001 and two side portions of the corresponding peak of the first guide surface 1010). Alternatively, the shape of the valleys on the first matching surface 1001 is required to be configured such that when valleys of the first matching surface 1001 are in contact with the peaks of the first guide surface 1010, the first transmission disk 1100 is also into engagement with the second transmission disk 1200. For example, the shape of the valley of the first matching surface 1001 is complementary to that of the peak of the first guide surface 1010. In this case, when the first transmission disk 1100 is engaging the second transmission disk 1200, the peaks of the first guide surface 1010 fit in valleys of the first matching surface 1001.

With continued reference to FIG. 7e, the first engagement components 1020 and the third engagement components 1050 are alternatively arranged on the second transmission disk 1200. This can result in an increased axial size utilization of the second transmission disk 1200.

Figure 7G:
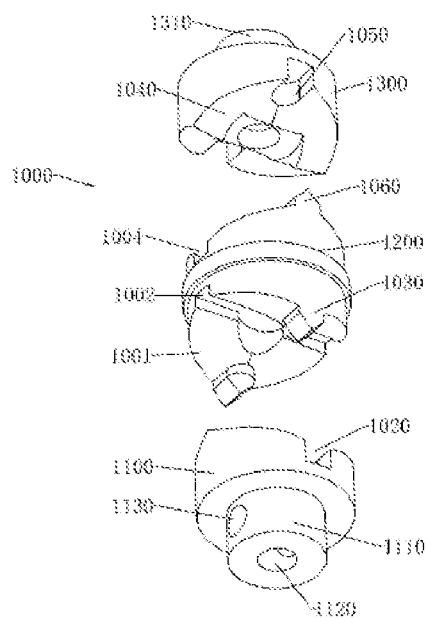
Figure 7H:
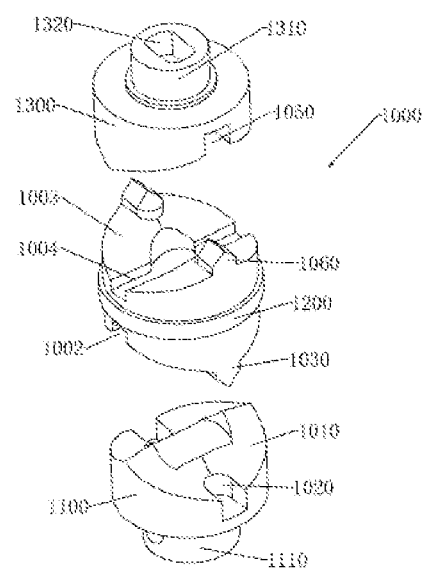
FIG. 7h is a schematic exploded view of the transmission assembly of FIG. 7g taken from another direction.

Reference is now made to FIGS. 7g and 7h, which schematically illustrate the structure of a further variant of embodiment 1. As shown in FIGS. 7g and 7h, the first guide surface 1010 is formed on the second end of the first transmission disk 1100, the first matching surface 1001 formed on the third end of the second transmission disk 1200, the second matching surface 1003 formed on the fourth end of the second transmission disk 1200, the second guide surface 1040 formed on the fifth end of the third transmission disk 1300. In this embodiment, each of the first matching surface 1001 and the second matching surface 1003 is provided thereon with two peaks and two valleys, and the peaks of the first matching surface 1001 and peaks of the second matching surface 1003 are arranged at the same circumferential positions. Of course, the peaks of the first matching surface 1001 and peaks of the second matching surface 1003 may be arranged at the different circumferential positions, such as in an alternative arrangement.

In alternative embodiments, the first matching surface may be further formed at the second end of the first transmission disk, the first guide surface formed at the third end of the second transmission disk, the second guide surface formed at the fourth end of the second transmission disk. The second matching surface is formed at the fifth end of the third transmission disk (not shown).

Figure 8A:
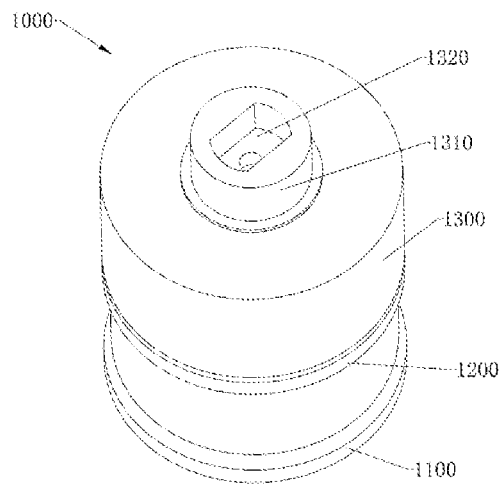
FIG. 8a is a structural schematic of the transmission assembly according to embodiment 2 of present disclosure.
Figure 8B:
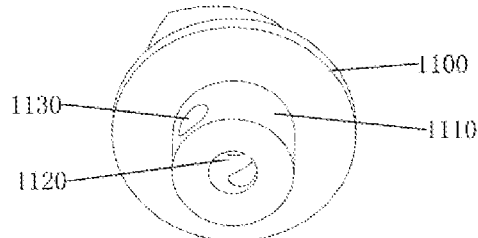
FIG. 8b is a structural schematic of a first transmission disk of the transmission assembly of FIG. 8a taken from one direction.
Figure 8C:
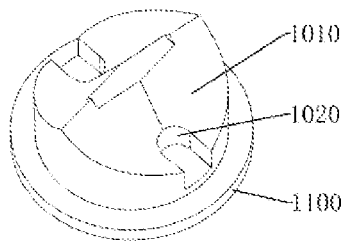
FIG. 8c is a structural schematic of the first transmission disk of FIG. 8b taken from another direction.
Figure 8D:
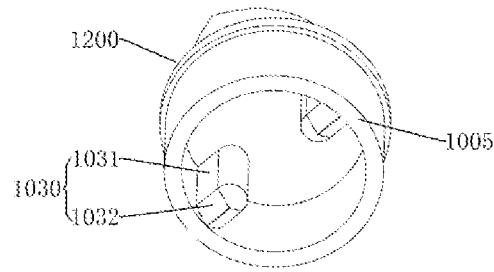
FIG. 8d is a structural schematic of a second transmission disk of the transmission assembly of FIG. 8a taken from one direction.
Figure 8E:
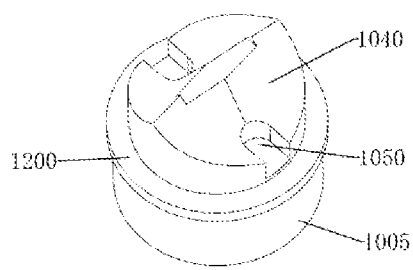
FIG. 8e is a structural schematic of the second transmission disk of FIG. 8d taken from another direction.
Figure 8F:
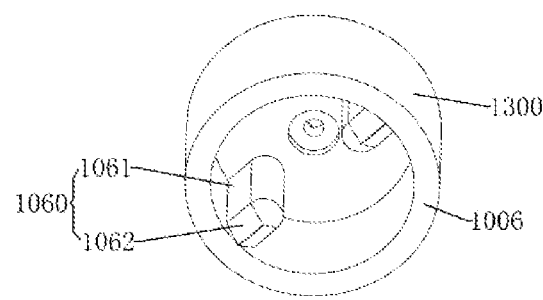
FIG. 8f is a structural schematic of a third transmission disk of the transmission assembly of FIG. 8a taken from one direction.
Figure 8G:
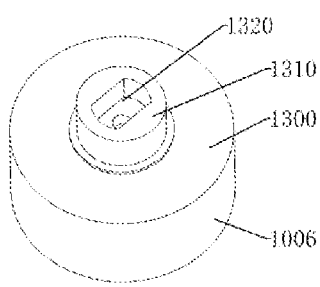
FIG. 8g is a structural schematic of the third transmission disk of FIG. 8f taken from another direction.

Reference is now made to FIGS. 8a to 8g. FIG. 8a is a structural schematic of the transmission assembly 1000 according to embodiment 2. FIGS. 8b and 8c are structural schematics of the first transmission disk 1100. FIGS. 8d and 8e are structural schematics of the second transmission disk 1200. FIGS. 8f and 8g are structural schematics of the third transmission disk 1300.

As shown in FIG. 8b, the first end of the first transmission disk 1100 may be configured to couple a driving mechanism. Therefore, the structures of these may be the same as in embodiment 1, and a detailed description thereof is omitted. FIG. 8c schematically illustrates the structure of the second end of the first transmission disk 1100. As shown in FIG. 8c, a first guide surface 1010 is formed at the second end of the first transmission disk 1100, and the first guide surface 1010 is projected on the reference plane to obtain a projection circle. Such projection circle has a diameter less than a diameter of a projection circle of the first transmission disk 1100 on the reference plane. First engagement components 1020 are provided on the first guide surface 1010.

As shown in FIG. 8d, second engagement components 1030 are provided on the third end of the second transmission disk 1200, and the first shield wall 1005 surrounding the second engagement components 1030 are provided on the end face of the third end. The first shield wall 1005 is annular and may be sleeved over the first guide surface 1010. Further, the second engagement components 1030 are situated in and fixedly connected to the first shield wall 1005. An inner diameter of the first shield wall 1005 may be greater than or equal to the diameter of the projection circle of the first guide surface 1010 on the reference plane and is less than the diameter of the projection circle of the first transmission disk 1100 on the reference plane. Preferably, a wall thickness of the first shield wall 1005 may be equal to the difference value between the diameters of the projection circles of the first guide surface 1010 and the first transmission disk 1100. As such, when the first engagement components 1020 come into engagement with the second engagement components 1030, the end where the first guide surface 1010 is situated is inserted in the first shield wall 1005, while an end of the first shield wall 1005 away from the second transmission disk 1200 abuts against the first transmission disk 1100.

As shown in FIG. 8e, the second guide surface 1040 is formed on the fourth end of the second transmission disk 1200. The second guide surface 1040 is projected on the reference plane to obtain a projection circle. This projection circle has a diameter less than a diameter of the projection circle of the second transmission disk 1200 on the reference plane. Third engagement components 1050 are provided on the second guide surface 1040.

As shown in FIG. 8f, fourth engagement components 1060 is provided on fifth end of the third transmission disk 1300. The second shield wall 1006 surrounding the fourth engagement components 1060 are further provided on the fifth end. The second shield wall 1006 is annular and may be sleeved over the second guide surface 1040. Further, the fourth engagement component 1060 are situated in and fixedly connected to the second shield wall 1006. An inner diameter of the second shield wall 1006 is greater than or equal to the diameter of the projection circle of the second guide surface 1040 and is less than the diameter of the projection circle of the second transmission disk 1200 on the reference plane. Preferably, a wall thickness of the second shield wall 1006 may be equal to the difference value between the diameters of the projection circles of the second guide surface 1040 and the second transmission disk 1200. As such, when the third engagement components 1050 come into engagement with the fourth engagement components 1060, the end where the second guide surface 1040 is situated is inserted in the second shield wall 1006, while an end of the second shield wall 1006 away from the third transmission disk 1300 abuts against the second transmission disk 1200.

Since the second engagement components 1030 cooperates with the first shield wall 1005, when the second engagement components 1030 come into engagement with the respective first engagement components 1020 for transmission, the first shield wall 1005 improves stress conditions of the second engagement components 1030, reduces the invasion of dust or other foreign matter and extends the service life of the second engagement components 1030. Moreover, this arrangement further allows to reduce weight of the second transmission disk 1200 and simplify the structure of the second transmission disk 1200. Likewise, the second shield wall 1006 can help extend the service life of the fourth engagement components 1060 and reduce the weight of the third transmission disk 1300.

Figure 9A:
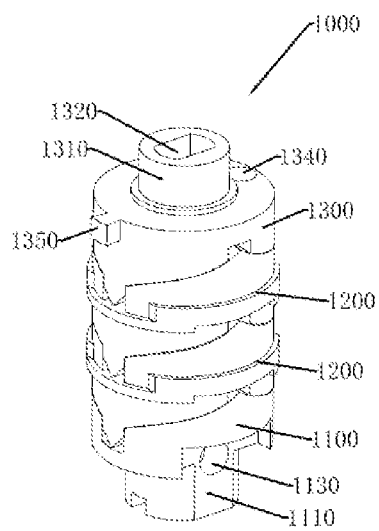
FIG. 9a is a structural schematic of the transmission assembly according to embodiment 3 of present disclosure.
Figure 9B:
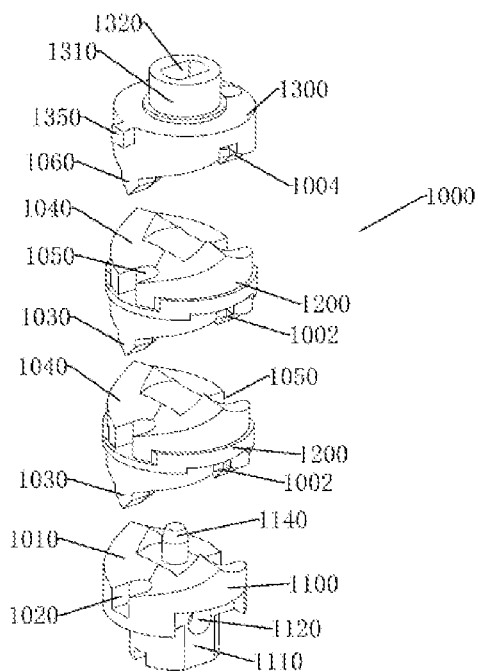

FIGS. 9a and 9b are structural schematics of the transmission assembly 1000 according to embodiment 3. A plurality of sterile assemblies 200 may be needed in the application requiring multilayer protection. For a surgical instrument system including a plurality of sterile assemblies 200, the transmission assembly 1000 may accordingly include a plurality of second transmission disks 1200. In the embodiment shown in FIGS. 9a and 9b, two second transmission disks 1200 are provided. Further, the two second transmission disks 1200 are identical, and each of them has third and fourth ends that are different in structure. For example, in this embodiment, for each second transmission disk 1200, the first matching surface 1001 is formed on the third end and the second engagement components 1030 are provided on the first matching surface 1001. Additionally, for each second transmission disk 1200, the second guide surface 1040 is formed on the fourth end, and third engagement components 1050 are provided on the second guide surface 1040. As such, the second engagement components 1030 of one second transmission disk 1200 can engage the third engagement components 1050 of the other second transmission disk 1200, thus achieving the coupling of the two second transmission disks 1200. Correspondingly, a first guide surface 1010 is formed on the second end of the first transmission disk 1100, and a second matching surface 1003 is formed on the fifth end of the third transmission disk 1300, the fourth engagement components 1060 provided on the third matching surface 1003. In this way, the transmission assembly 1000 can be assembled in the same manner as in the above embodiments. It is to be understood that it is also possible to have the first guide surface 1001 formed on the end face of third end of the second transmission disks 1200 and the fourth engagement component 1060 provided on the end face of the fourth end. In one alternative embodiment, the two second transmission disks are different, but each of them is structured identically at the third and fourth ends. For example, the second transmission disk proximal to the first transmission disk 1100 has its third and fourth ends each provided with a matching surface, and the second transmission disk away from the first transmission disk 1100 has its third and fourth ends each with a guide surface.

Figure 10:
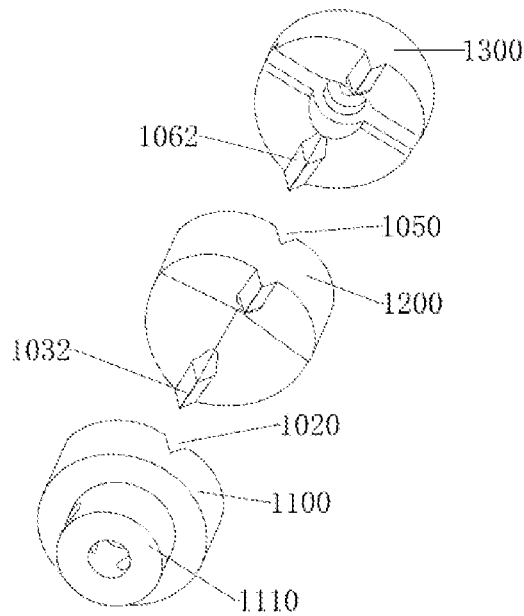
FIG. 10 is a structural schematic of the transmission assembly according to embodiment 4 of present disclosure.

FIG. 10 is a structural schematic of the transmission assembly 1000 according to embodiment 4. As shown in FIG. 10, in this embodiment, the second engagement component includes a first guide portion 1032 but no first driving force transmission portion. The structure of the fourth engagement component is similar to that of the second engagement component 1030, i.e., the fourth engagement component do not include a second driving force transmission portion. Specifically, two first engagement components 1020 are provided on the end face of the second end of the first transmission disk 1100 and two second engagement components 1030 are provided on the end face of the third end of the second transmission disk 1200. The second engagement component includes a first guide portion 1032, which is directly disposed on the end face of the second end of the first guide portion 1032. Similarly, two third engagement components 1050 are provided on the end face of the fourth end of the second transmission disk 1200 and two fourth engagement components are provided on the end face of the fifth end of the third transmission disk 1300. The fourth engagement component includes a second guide portion 1062 directly connected to the end face of the fifth end. In this case, the first 1020 and third 1050 engagement components match the first 1032 and second 1062 guide portions both in shape and size. This allows sufficient surface contact between the engagement components and the guide portions to increase mutual friction, imparting both torque transmission and guide capabilities to the guide portions.

Apparently, for a surgical instrument system not including any sterile assembly, the transmission assembly includes the first transmission disk and the second transmission disk arranged in sequence. The first transmission disk is similar to the first transmission disk 1100 of the above embodiments. Additionally, the end face of the third end of the second transmission disk is similar to the end face of the third end of the second transmission disk 1200 in the above embodiments, and the end face of the fourth end is similar to the end face of the sixth end of the third transmission disk. Therefore, a detailed description thereof is omitted.

Figure 2C:
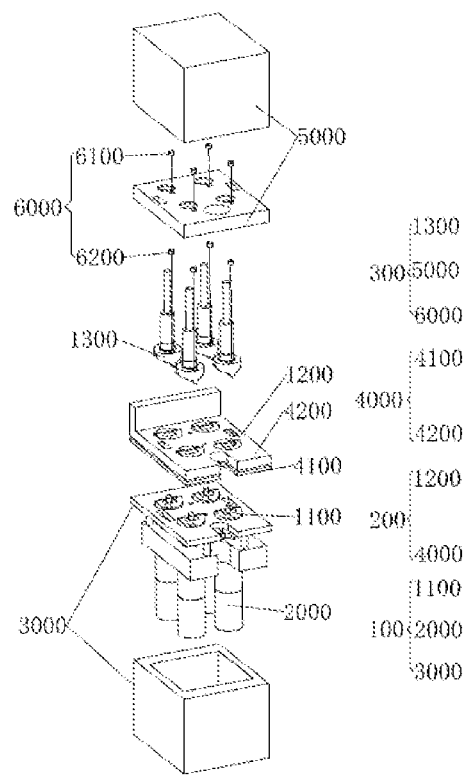
FIG. 2c is a schematic exploded view of the surgical instrument system of FIG. 2a, in which some elements are not shown.

Base on the above-described transmission assembly 1000, the second object of present disclosure is to provide a surgical instrument system for use in a surgical robot. Referring to FIGS. 2a to 2c, in connection with FIG. 5a, the surgical instrument system includes a driving force box, a sterile plate 4000, a surgical instrument 300 and a transmission assembly 1000 as described above. The driving force box includes a driving mechanism 2000 and a first box body 3000. The driving mechanism 2000 is disposed in the first box body 3000, and at least one output hole (not labeled in the figures) is provided in the first box body 3000. At least one sterile plate 4000 is provided, each provided thereon with at least one transmission hole (not labeled in the figures). The surgical instrument 300 includes an instrument box, an instrument shaft 320 and an instrument terminal 310. Further, the instrument box includes a second box body 5000 and a transmission module (not labeled in the figures). The transmission module is disposed in the second box body 5000 and is coupled to the instrument shaft 320 and/or the instrument terminal 310 so as to drive the instrument shaft 320 and/or the instrument terminal 310 to move. Moreover, at least one input hole is provided in the second box body 5000. The first box body 3000, the sterile plate 4000 and the second box body 5000 are arranged in series and the output holes are arranged coaxially with the corresponding transmission holes and the input holes. The first transmission disk 1100 is disposed in the output hole, with its first end coupled to the driving mechanism 2000. The second transmission disk 1200 is disposed in the transmission hole, and the third transmission disk 1300 is disposed in the input hole with its sixth end coupled to the transmission module. In general, the number of the driving mechanisms 2000 and the number of the transmission assemblies 1000 are determined by freedoms of movement of the surgical instrument 300. The driving force box and the first transmission disk 1100 constitute the driving assembly 100. The sterile plate 4000 and the second transmission disk 1200 constitute a sterile assembly 200. The instrument box and the third transmission disk 1300 constitute an instrument box assembly.

When the first engagement components 1020 are into engagement with the second engagement components 1030 and the third engagement components 1050 are into engagement with the fourth engagement components 1060, driving force provided by the driving mechanism 2000 can be transferred by the transmission assembly 1000 to the transmission module, which in turn drives various joints of the instrument terminal 310 to move. For example, the instrument terminal 310 includes an end effector and joints controlling the end effector to yaw and/or pitch. The end effector may include an opening-closing joint. Specific examples of the end effector may include, but are not limited to, forceps, scissors, graspers, needle holders, cutting blades, staplers, etc. The instrument terminal 310 may further include a snake-like joint at a proximal end of the end effector to enable adjustments of the end effector within a wider range in a more flexible manner.

Before the surgical instrument system is assembled, the first transmission disk 1100, the second transmission disk 1200 and the third transmission disk 1300 may be oriented arbitrarily. However, when the assembling of the surgical instrument system is completed, each of the first transmission disk 1100, the second transmission disk 1200 and the third transmission disk 1300 should be oriented in a predetermined orientation. Here, the predetermined orientation is referred to as a "zero position", and any other orientation is referred to as a "non-zero position". In practice, the zero position may be defined by a user as actually required. For example, as shown in FIG. 2a, in which assembling of the surgical instrument system is completed and the transmission module is coupled to the instrument terminal 310 through the instrument shaft 320, the orientation which the first transmission disk 1100, second transmission disk 1200 and third transmission disk 1300 are located is defined as the zero position when the instrument terminal 310 is collinear with or parallel to the instrument shaft 320. Further, some positions that are unfavorable to the assembly or to rotation of the transmission disks, for example, the position where the second engagement component 1030 is in contact with the peak of the first guide surface 1010, and the position where the fourth engagement component 1060 is in contact with the peak of the second guide surface 1040. These positions are referred to as the "worst position" of the transmission assembly 1000.

As shown in FIG. 2c, the surgical instrument system (more exactly, the instrument box assembly) may further include at least one position correction magnet set 6000 for helping the third transmission disk 1300 reach the zero position. Specifically, the position correction magnet set 6000 includes a first magnet 6100 and a second magnet 6200, the first magnet 6100 disposed on the second box body 5000, the second magnet 6200 disposed on the third transmission disk 1300. This embodiment is not limited to any particular locations where the first magnet 6100 and the second magnet 6200 are disposed, as long as that the first magnet 6100 and the second magnet 6200 are attract each other and the attractive force between the first magnet 6100 and the second magnet 6200 along the whole circumference reaches its maximum value when the third transmission disk 1300 is in its zero position.

For the third transmission disk 1300, the second magnet 6200 may be disposed at the sixth end. As shown in FIG. 5g, a receiving hole 1340 for receiving the second magnet 6200 may be provided on the sixth end of the third transmission disk 1300.

Figure 3:
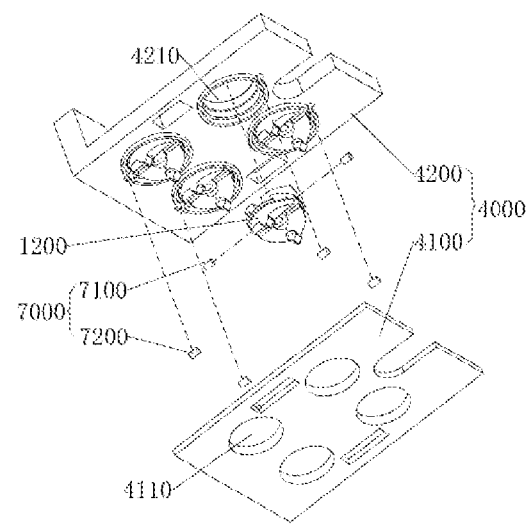
FIG. 3 schematically illustrates the surgical instrument system of FIG. 2a, in which the sterile substrate, sterile substrate and position correction magnet set are disassembled.

Optionally, the surgical instrument system may further include at least one anti-dislocation magnet set 7000 (specifically, the sterile assembly 200 include the anti-dislocation magnet set 7000). The anti-dislocation magnet set 7000 is configured to avoid the transmission assembly 1000 from reaching the worst position. As shown in FIG. 3, the anti-dislocation magnet set 7000 includes a third magnet 7100 and a fourth magnet 7200. The third magnet 7100 may be disposed on a circumferential side wall of the second transmission disk 1200, and the fourth magnet 7200 may be disposed on the wall of the transmission hole. When the transmission assembly 1000 is in the worst position, the third magnet 7100 and the fourth magnet 7200 repel each other, and the repulsive force causes the second transmission disk 1200 to rotate and keep off the worst position.

Optionally, the surgical instrument system further includes a circumferential limiter configured to limit a range of rotation of the third transmission disk 1300 (Specifically, the instrument box assembly includes the circumferential limiter). The circumferential limiter may include a limiting protrusion 1350 provided on a circumferential side wall of the third transmission disk 1300. A slide groove (not shown) for fitting with the limiting protrusion 1350 may be provided in the second box body 5000. The limiting protrusion 1350 may be provided in and slidable along the slide groove. Through providing the circumferential limiter, the rotational angle of the third transmission disk 1300 can be accurately controlled, which in turn enables to ensure the safety during use of the surgical instrument.

Figure 4:
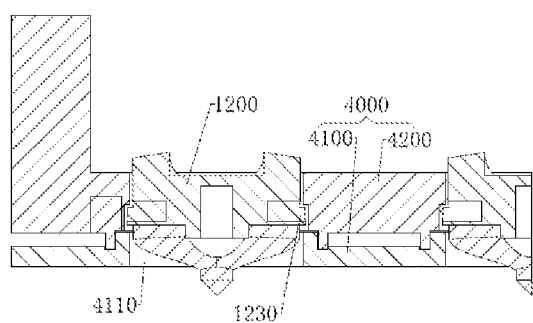
FIG. 4 is a partial cross-sectional view of a sterile assembly according to an embodiment of the present disclosure.

Optionally, the surgical instrument system further includes an axial limiter configured to prevent the second transmission disk 1200 from dislodging from the sterile plate 4000. Referring to FIG. 4, the sterile plate 4000 includes a sterile substrate 4100 and a sterile cover 4200. The sterile substrate 4100A is provided thereon with a first through hole 4110, and the sterile cover 4200 is provided thereon with a second through hole 4210. The second through hole 4210 and the first through hole 4110 constitutes the transmission hole. Further, the sterile cover 4200 is detachably attached to the sterile substrate 4100, and the sterile substrate 4100 is detachably attached to the driving force box (e.g., by snapping). A limiting collar 1230 is provided on the circumferential side wall of the second transmission disk 1200, and the second through hole 4210 in the sterile cover 4200 has a varying inner diameter. Specifically, the section of the second through hole 4210 close to the first through hole 4110 has an inner diameter greater than each of an inner diameter of a section of the second through hole 4210 away from the first through hole 4110 and an inner diameter of the first through hole 4110. Further, the inner diameter of the section of the second through hole 4210 close to the first through hole 4110 matches the outer diameter of the limiting collar 1230, and the inner diameter of the section of the second through hole 4210 away from the first through hole 4110 matches the outer diameter of the second transmission disk 1200. In this way, the first through hole 4110 and the second through hole 4210 together define a limiting recess in which the limiting collar 1230 is situated, so that the second transmission disk 1200 does not dislodge from the transmission hole. In other words, the limiting recess and the limiting collar 1230 constitute the axial limiter together. In this embodiment, the limiting collar 1230 may be a continuous rib running along the circumference of the second transmission disk 1200, or may consist of multiple rib segments spaced along the circumference of the second transmission disk 1200.

Typically, before the driving mechanism 2000, the first transmission disk 1100, the second transmission disk 1200, the third transmission disk 1300 and the surgical instrument 300 are assembled, each of them is in a non-zero position. After they are assembled, each of the driving mechanism 2000, the first transmission disk 1100, the second transmission disk 1200, the third transmission disk 1300 and the surgical instrument 300 should be in its zero position. Here, the metrological term "zero position" is the benchmark for measuring the intraoperative motion parameters (e.g., direction, displacement, angle, etc.) of the transmission disk, the surgical instrument, or the like. Typically, when the surgical instrument 300 is in the zero position, the instrument terminal 310 is collinear with or parallel to an axis of the instrument shaft 320. A detailed description of the assembly of the surgical instrument system is set forth below.

First of all, as an encoder (not shown) is provided on the driving mechanism 2000, the position information of the first transmission disk 1100 can be obtained via the encoder after the system is powered on. The driving mechanism 2000 then drives the first transmission disk 1100 to rotate into its zero position. This process may be controlled by a predefined program. Upon reaching the zero position, the first transmission disk 1100 is maintained in the position. After that, the second transmission disk 1200 can be engaged to the first transmission disk 1100 from any orientation and directly reaches its zero position.

Subsequently, the second transmission disk 1200 is engaged to the first transmission disk 1100. The second transmission disk 1200 in a non-zero position comes into contact with the first transmission disk 1100 under the action of an external force. Afterward, the second engagement component 1030 slides along the first guide surface and accurately gets into the first engagement component 1020 to engage the first engagement component 1020. At this time, the second transmission disk accurately rotates to its zero position.

After that, position of the instrument terminal 310 is adjusted. Referring to FIG. 2b, the surgical instrument includes the instrument terminal 310 and instrument shaft 320 that are connected each other. The instrument terminal 310, for example, is a forcep. Before the assembly of the surgical instrument system, it is needed to sleeve the instrument shaft 320 into the trocar 400 that is placed at an incision of the human body, so that the instrument terminal 310 of the surgical instrument 300 in the surgical instrument system can be inserted into human body.

Since an inner diameter of the trocar 400 is comparable to an outer diameter of the instrument terminal 310, in order to successfully inserts forcep into the trocar 400, the forcep must be straighten to enable its symmetry axis collinear with the axis of the instrument shaft 320. In this process, the third transmission disk 1300 will be forced to rotate. When the symmetry axis of the forcep is collinear with the axis of the instrument shaft 320, the third transmission disk 1300 reaches its zero position. However, in practice, manual adjustment can only locate the third transmission disk 1300 roughly at its zero position.

Therefore, the third transmission disk 1300 comes into contact with the second transmission disk 1200 under the action of an external force. Afterward, the fourth engagement component 1060 slides along the second guide surface and accurately gets into the third engagement component 1050 to engage the third engagement component 1050. At this time, the third transmission disk 1300 accurately rotates to its zero position.

Further, it is to be noted that, although the orientation information of the first transmission disk 1100 can be measured before the surgical instrument system is assembled, it is unable to obtain the orientation information of the third transmission disk 1300. When the second transmission disk 1200 and the third transmission disk 1300 are assembled as the steps described above, the third transmission disk 1300 may be manually adjusted to located roughly at its zero position with a certain angular deviation. When this angular deviation is less than the fault-tolerant angle, the third transmission disk 1300 can enable the instrument get to zero exactly.

The fault-tolerant angle is in relation to the number of the engagement components on the third transmission disk

1300. Taken the third transmission disk 1300 provided thereon with two fourth engagement components 1060 (i.e., four first guide surfaces 1010 are provided) as an example, the tolerated angular deviation of the third transmission disk 1300 relative to the zero position is greater than ±90°. In this case, the fourth engagement components 1060 can successfully slide into and thus come into engagement with the third engagement components 1500, as long as the fourth engagement components 1060 are located between the two peaks. Here, the angle between adjacent peaks is called as the fault-tolerant angle. The fault-tolerant angle in this example is 180°. Indeed, the fault-tolerant angle is equal to 360°/N, where N represents the number of the fourth engagement components 1060. When the angular deviation is within the range of the fault-tolerant angle, the instrument terminal 310 can maintain the same posture during multiple assembly processes of the surgical instrument system. Such a characteristic facilitates the determination of absolute position information of individual transmission disks after the surgical instrument system is assembled, thus enabling to ensure safety of the surgical operation.

The third object of present disclosure is to provide a surgical robot including a surgical instrument system as described above. Further, the surgical robot further includes a robotic arm for holding the surgical instrument system. The driving assembly 100 is secured to the robotic arm terminal. For example, the robotic arm terminal includes a moveable joint, and the driving assembly 100 is disposed on the moveable joint and moves with movements of the moveable joint. The sterile assembly 200 is provided on a sterile bag and is detachably coupled to the driving assembly 100. The surgical instrument is detachably coupled to the sterile assembly 200 via the instrument box assembly.

In an alternative embodiment, the surgical robot may be integrally sterilized using a special sterilization method (e.g., ozone sterilization, hydrogen peroxide sterilization, etc.). In this case, the surgical instrument system may include the driving assembly 100 and the surgical instrument 300. Accordingly, the transmission assembly is connected to the transmission interfaces provided in the driving assembly 100 to constitute the transmission assembly, so as to directly transfer the driving force provided by the driving assembly 100 directly to the instrument box assembly.

The fourth object of present disclosure is to provide a driving assembly 100. The driving assembly 100 includes: a driving mechanism 2000 and a first box body 3000 configured to accommodate the driving mechanism 2000 and provided thereon with at least one output hole (not labeled in figures); and at least one transmission disk that engages with another transmission disk including another engagement component. The transmission disk is rotatably disposed in the output hole and has two opposing end parts, one of which is coupled to the driving mechanism 2000, and the other one of which has a guide surface formed on the end face thereof. Moreover, at least one engagement component is provided on the guide surface, and the guide surface is configured to cause another engagement component to move along the guide surface and get into engagement with the at least one engagement component. In an alternative embodiment, the driving assembly 100 includes one transmission disk that engages with another transmission disk including another engagement component and another guide surface. The transmission disk is disposed in the output hole and has two opposing end parts. One of the two opposing end parts is coupled to the driving mechanism 2000, and the other one of the two opposing end parts has at least one engagement component formed on the end face thereof. The engagement component is configured to move along the guide surface of another transmission disk and gets into engagement with the engagement component of another transmission disk.

Figure 11:
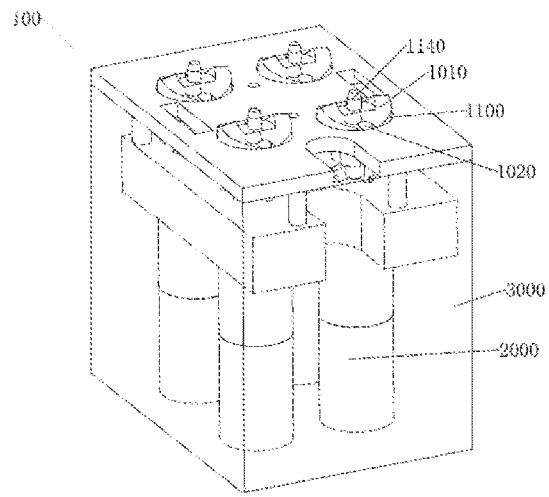
FIG. 11 is a structural schematic of a driving box according to an embodiment of present disclosure.

As shown in FIG. 11, in one embodiment, the transmission disk may be the first transmission disk 1100 and another transmission disk may be the second 1200 or third 1300 transmission disk. The first end of the first transmission disk 1100 is configured to couple the driving mechanism 2000. For example, a first coupling post 1110 is provided on the first end, and a first coupling hole 1120 configured for receiving the output shaft of the driving mechanism is provided in the first coupling post 1110. Additionally, a locking hole 1130 communicating with the first coupling hole 1120 is provided in a side wall of the first coupling post 1110. The locking hole 1130 is configured to cause the output shaft of the driving mechanism to rotate in synchronization with the first transmission disk 1100. A first guide surface 1010 is formed on the second end of the first transmission disk 1100. The first guide surface 1010 has two peaks and two valleys that are arranged along the circumference of the end face where the first guide surface 1010 is situated.

Two first engagement components 1020 are provided on the first guide surface 1010. The first engagement component 1020 is a recess provided at a corresponding valley. The first guide surface 1010 configured such that the second engagement component of the second 1200 or third 1300 transmission disk slides along the first guide surface until it comes into engagement with the first engagement components 1020 to achieve the transfer of a torque.

Figure 12:
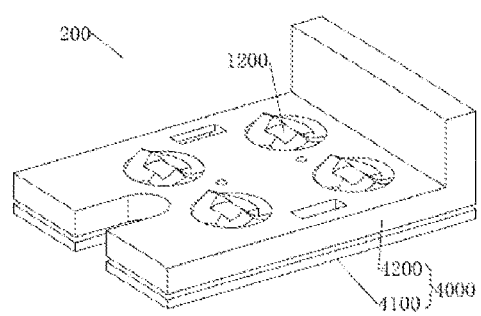
FIG. 12 is a structural schematic of a sterile assembly according to an embodiment of present disclosure.

The fifth object of present disclosure is to provide a sterile assembly 200. Referring to FIG. 12, the sterile assembly 200 includes: at least one sterile plate 4000 provided with at least one transmission hole; at least one transmission disk that engages with another transmission disk including another engagement component, the transmission disk rotatably disposed in the transmission hole and has two opposing end parts. At least one of the two opposing end parts has a guide surface formed on the end face thereof, and the guide surface is provided thereon with at least one engagement component. The guide surface is configured such that another engagement component moves along the guide surface until it comes into engagement with at least one engagement component. In an alternative embodiment, in addition to the sterile plate 4000 provided with at least one transmission hole, the sterile assembly 200 further includes at least one transmission disk that engages with another transmission disk including a guide surface and another engagement component provided on the guide surface. The at least one transmission disk is rotatably disposed in the transmission hole and has two opposing end parts. An engagement component is formed at least one of the two end parts. The engagement component is configured to move along the guide surface and come into engagement with the another engagement component.

Figure 13:
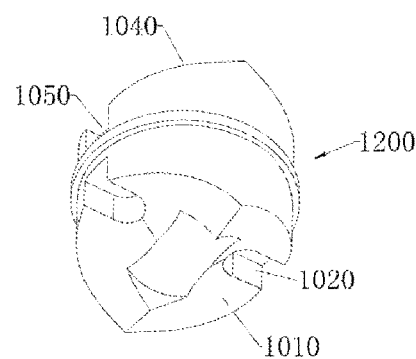
FIG. 13 is a structural schematic of a transmission disk in the sterile assembly of FIG. 12, in which two end faces of the transmission disk each are formed as a guide surface.

Specifically, the transmission disk may be the second transmission disk 1200. The second transmission disk 1200 is configured to engage with each of the first transmission disk 1100 and the third transmission disk 1300. In one embodiment, as shown in FIG. 13, a guide surface is formed on each of the end faces of the two ends of the second transmission disk 1200, and an engagement component is provided on each guide surface. Accordingly, another engagement components are provided on end faces of the first transmission disk 1100 and the third transmission disk 1300. That is, a second engagement component 1030 is provided on the end face of the second end of the first transmission disk 1100 and a fourth engagement component 1060 is provided on the end face of the fifth end of the third transmission disk 1300. A first guide surface 1010 may be formed on the end face of the third end of the second transmission disk 1200, and at least one first engagement component 1020 configured to engage with the second engagement component 1030 may be provided on the first guide surface 1010. The first engagement component 1020 is preferred to be a recess. A second guide surface 1040 is provided on the end face of the fourth end of the second transmission disk 1200, and at least one third engagement component 1050 configured to engage with the fourth engagement component may be provided on the second guide surface 1040. The third engagement component 1050 is preferred to be a recess. The first guide surface 1010 is configured such that the second engagement component 1030 moves along the first guide surface 1010 until it comes into engagement with the first engagement component 1020 to allow the transfer of a torque between the first transmission disk 1100 and the second transmission disk 1200. The second guide surface 1040 is so configured that the fourth engagement component 1060 can move thereon into engagement with the third engagement component 1050 to enable torque transmission between the second transmission disk 1200 and the third transmission disk 1300.

With continued reference to FIG. 4, the sterile plate 4000 includes a sterile substrate 4100 and a sterile cover 4200. A first through hole 4110 is provided in the sterile substrate 4100, and a second through hole 4210 is provided in the sterile cover 4200. The second through hole 4210 and the first through hole 4110 constitute the transmission hole together. Further, the sterile cover 4200 is detachably attached to the sterile substrate 4100. The sterile cover 4200 can prevent the transmission disk from dislodging from the sterile substrate 4100. Additionally, a limiting collar 1230 is provided on the circumferential side wall of the second transmission disk 1200, and the second through hole 4210 in the sterile cover 4200 has a varying inner diameter. Specifically, the section of the second through hole 4210 close to the first through hole 4110 has an inner diameter greater than each of an inner diameter of the section of the second through hole 4210 away from the first through hole 4110 and an inner diameter of the first through hole 4110. Further, the inner diameter of the section of the second through hole 4210 close to the first through hole 4110 matches an outer diameter of the limiting collar 1230, and the inner diameter of the section of the second through hole 4210 away from the first through hole 4110 matches an outer diameter of the second transmission disk 1200. Moreover, the inner diameter of the first through hole 4110 also matches the outer diameter of the second transmission disk 1200. In this way, the first through hole 4110 and the second through hole 4210 together define a limiting recess in which the limiting collar 1230 is situated, so that the second transmission disk 1200 does not dislodge from the transmission hole.

Figure 14:
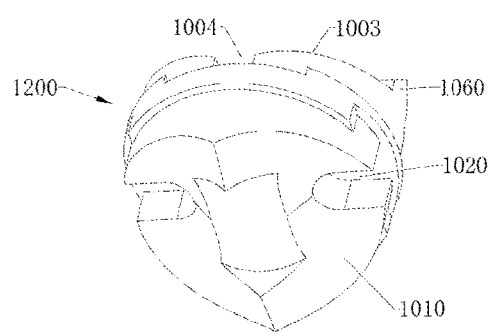
FIG. 14 is a structural schematic of a transmission disk in the sterile assembly of FIG. 12, in which one end face of the transmission disk is formed as a guide surface and the other end face of transmission disk is formed as a matching surface.

In an alternative embodiment, as shown in FIG. 14, a guide surface is formed on the end face of one end of the second transmission disk 1200, and at least one first engagement component 1020 each implemented as a recess is provided on the guide surface. For example, the first guide surface 1010 is provided on the end face of the third end of the second transmission disk 1200. At least one first engagement component 1020 each implemented as a recess is provided on the first guide surface 1010, and at least one fourth engagement component 1060 each implemented as a protrusion is provided on the end face of the fourth end of the second transmission disk 1200. In this case, a second matching surface 1003 may be provided on the end face of the fourth end, and the fourth engagement component 1060 is provided on the second matching surface 1003.

Figure 15:
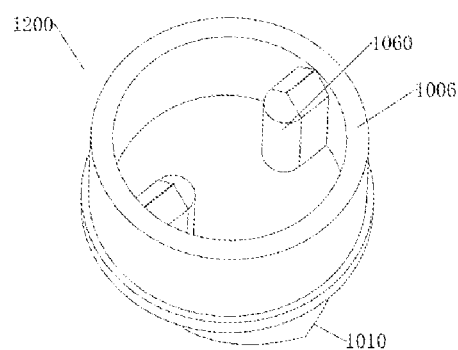
FIG. 15 is a structural schematic of a transmission disk in the sterile assembly of FIG. 12, in which one end face of the transmission disk is formed as a guide surface, and the other end face of transmission disk has a shield wall formed thereon.

Of course, in an alternative embodiment as shown in FIG. 15, an annular second shield wall 1006 surrounding and connected to the fourth engagement component 1060 may be provided on the end face of the fourth end.

Further, it is to be understood that, in this embodiment, the second transmission disk may have a second guide surface formed on the end face of the fourth end and a second engagement component provided on the end face of the third end. As such, a first matching surface may be formed on the end face of the third end. Alternatively, an annular first shield wall (not shown) surrounding and coupled to the second engagement component is provided on the end face of the third end of the second transmission disk.

Further, the second and fourth engagement components are provided on the end faces of opposing ends of the second transmission disk 1200, respectively. The second engagement component is configured to move along the first guide surface and get into engagement with the first engagement component on the first guide surface to achieve the transfer of a torque between the first and second transmission disks. The fourth engagement component is configured to move along the second guide surface and get into engagement with the third engagement component on the second guide surface to achieve the transfer of a torque between the second and third transmission disks.

Figure 16:
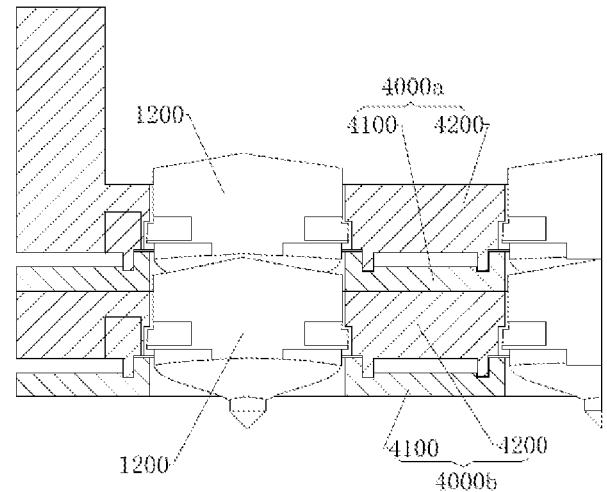
FIG. 16 is a structural schematic of a sterile assembly according to an embodiment of present disclosure, in which two sterile plates are arranged.

Further, the first engagement component 1020 can fit with the fourth engagement component 1060, so that the first engagement component 1020 can engage with the fourth engagement component 1060. Based on this, the sterile assembly 200 may include two sterile plates 4000, which are detachably attached to each other. As shown in FIG. 16, the two sterile plates 4000 are a first sterile plate 4000a and a second sterile plate 4000b. The first sterile plate 4000a and second sterile plate 4000b may be identically structure and each include a sterile substrate 4100 and a sterile cover 4200 detachably coupled to the sterile substrate 4100. This sterile assembly is suitable for cases that need multilayer sterile protection. It is to be understood that while the sterile assembly has been described herein as including two sterile plates 4000 as an example, in practical use, it may also include three or more sterile plates 4000.

The sixth object of present disclosure is to provide an instrument box assembly for a surgical instrument 300 including an instrument shaft 320 and an instrument terminal 310. As shown in FIGS. 2a to 2c, the instrument box assembly includes an instrument box and a transmission disk for engaging with another transmission disk including another engagement component. The instrument box includes a second box body 5000 and a transmission module (not shown in figures). Further, the second box body 5000 includes a base, and at least one input hole is provided in the base. The transmission module is coupled to the instrument shaft 320 and/or the instrument terminal 310, so as to drive the instrument shaft 320 and/or the instrument terminal 310 to move. The transmission disk is rotatably disposed in the input hole and has two opposing end parts. One of the two end parts is coupled to the transmission module, and the other one of the two end parts has a guide surface formed on its end face. At least one engagement component is provided on the guide surface, and the guide surface is configured such that another engagement component on another transmission disk moves along the guide surface until it comes into engagement with the at least one engagement component. In an alternative embodiment, the transmission disk configured to cooperate with another transmission disk including a guide surface and another engagement component is disposed in the input hole and has two opposing end parts. One of the end parts is coupled to the transmission module, and the other one of the end parts has an engagement component provided on the end face thereof. The engagement component is configured to move along the guide surface and get into engagement with another engagement component.

Figure 17:
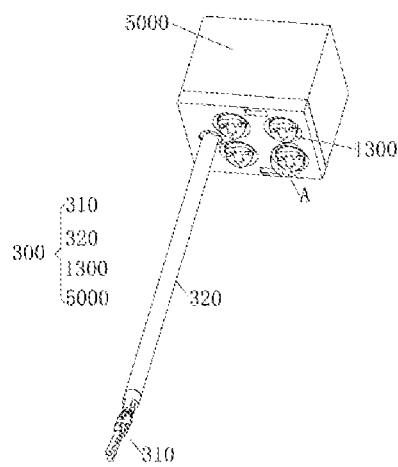
FIG. 17 is a structural schematic of a surgical instrument according to an embodiment of present disclosure.
Figure 18:
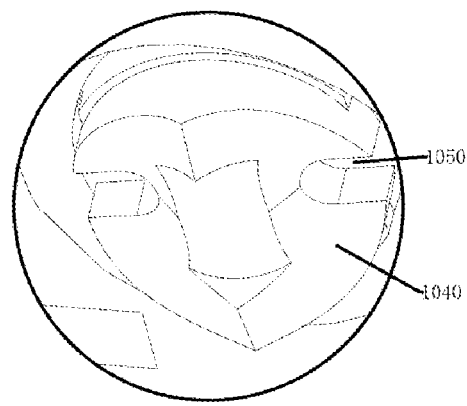
FIG. 18 is a schematic enlarged view of section A in FIG. 17.

Referring to FIGS. 17 and 18, in this embodiment, the transmission disk may be the third transmission disk 1300, and the another transmission disk may be the second transmission disk 1200 or the first transmission disk 1100. The third transmission disk 1300 has a second guide surface 1040 formed on the fifth end thereof, and at least one peak and at least one valley are circumferentially provided on the second guide surface 1040. A third engagement component 1050 is provided on the second guide surface 1040. Specifically, the third engagement component 1050 is a recess and provided at the valley.

As discussed above, the instrument terminal 310 includes a plurality of joints. The transmission module includes a rotating member, a flexible member and a group of guide pulleys. The flexible member is configured to couple the rotating member to a joint of the instrument terminal 410. The group of guide pulleys is configured to alter the extension direction of the flexible member. The rotating member is configured to drive joints of the instrument terminal 310 to move via the flexible member. Further, the instrument shaft 320 has one end coupled to the instrument terminal 310 and the other end rotatably coupled to the second box body 5000. The transmission module is further configured to drive the instrument shaft 320 to rotate about its own axis. This embodiment is not limited to any particular means for driving the instrument shaft 320 to rotate about its own axis. For example, the rotating member is coupled to the instrument shaft 320 by a gear. The sixth end of the third transmission disk 1300 is configured to pass through the input hole and couple the rotating member. Here, the third transmission disk 1300 may be coupled to the rotating member either detachably or integrally.

Further, the instrument box assembly also includes a circumferential limiter configured to restrain a range of rotation of the third transmission disk 1300. The circumferential limiter includes a limiting protrusion 1350 provided on a circumferential side wall of the third transmission disk 1300. Accordingly, a slide groove (not shown) is provided on the second box body 5000. The limiting protrusion 1350 cooperates with the slide groove to restrain a range of rotation of the third transmission disk 1300. Through providing the circumferential limiter, the rotational angle of the third transmission disk 1300 can be accurately controlled, which in turn enables to ensure the safety during use of the surgical instrument. Generally, the limiting protrusion 1350 is provided on a thick portion of the third transmission disk 1300 with a good stress condition.

Further, as shown in FIG. 2c, the instrument box assembly may further include a position correction magnet set 6000 for helping the third transmission disk 1300 reach its zero position. The position correction magnet set includes a first magnet 6100 and a second magnet 6200. The first magnet 6100 is disposed on the third transmission disk 1300, while the second magnet 6200 is provided on the second box body 5000. Further, the first magnet 6100 and the second magnet 6200 are configured such that a maximum magnetic attractive force is achieved between them when the third transmission disk 1300 is in its zero position.

Although the present disclosure has been disclosed hereinabove, it is not limited to the above disclosure. Those skilled in the art can make various changes and modifications to the disclosure without departing from the spirit and scope thereof. Accordingly, it is intended that any and all such changes and modifications also fall within the scope of the present disclosure as defined by the appended claims and equivalents thereof.

What is claimed is:

1. A transmission assembly for a surgical instrument, comprising a first transmission disk and a second transmission disk, wherein:

the first transmission disk has a second end, and the second transmission disk has a third end arranged face to face with the second end, one of an end face of the second end and an end face of the third end has a first guide surface formed thereon, and the other one of the end face of the second end and the end face of the third end is provided with a second engagement component, wherein at least one first engagement component is provided on the first guide surface, and the second engagement component is configured to be engageable with the first engagement component, and the second engagement component is configured to move along the first guide surface until the second engagement component is engaged with the first engagement component to allow a torque transfer between the first transmission disk and the second transmission disk, each of the second engagement components comprises a first guide portion, each first guide portion comprising two wedge surfaces that form a first intersection line;

wherein the first guide surface comprises a plurality of guide sub-surfaces that are connected in sequence, and adjacent guide sub-surfaces form a second intersection line at peaks of the first guide surface; and wherein the first and second intersection lines are configured such that when the second engagement components are in contact with the first guide surface at the peaks of the first guide surface, an axial projection of a first intersection line at least partially coincides with an axial projection of a corresponding second intersection lines; or the first and second intersection lines are configured such that when the second engagement components are in contact with the first guide surface at the peaks of the first guide surface, at least two of axial projections of a plurality of the first intersection lines are collinear and at least two of axial projections of a plurality of the second intersection lines are collinear.

2. The transmission assembly of claim 1, wherein the first guide surface has at least one peak and at least one valley that are circumferentially distributed along the end face of the end on which the first guide surface is formed, and the first engagement component is provided at the valley of the first guide surface, and wherein an axial projection of the first guide surface has a diameter greater than or equal to one tenth of a peak-to-valley axial distance of the first guide surface.

3. The transmission assembly of claim 1, wherein the second end of the first transmission disk is further provided with a locating pin extending axially, and the third end of the second transmission disk is further provided with a first locating hole extending axially, wherein the first locating pin and the first locating hole are configured to cooperate with each other to facilitate a concentric location of the first transmission disk and the second transmission disk.

4. The transmission assembly of claim 3, wherein the first engagement component is a recess, and the second engagement component is a protrusion, wherein a first shield wall surrounding the protrusion is provided on the end face where the second engagement component is provided, and the first shield wall is annular and connected with the protrusion; and wherein an axial projection of the end face where the first guide surface is situated has a diameter smaller than or equal to an inner diameter of the first shield wall.

5. The transmission assembly of claim 4, wherein the second engagement component comprises a first guide portion and a first driving force transmission portion, wherein the first guide portion is configured to contact with the first guide surface to guide the second engagement component to slide along the first guide surface, and the first driving force transmission portion is configured to transmit a driving force when the first engagement component is in engagement with the second engagement component.

6. The transmission assembly of claim 5, wherein:

each of an axial projection of the first engagement component and an axial projection of the first driving force transmission portion has a shape of a kidney ellipsoid, or each of the axial projection of the first engagement component and the axial projection of the first driving force transmission portion has a shape of a fan, and a fan formed by the first engagement component has an angle greater than or equal to an angle of a fan formed by the first driving force transmission portion.

7. The transmission assembly of claim 5, wherein at least two second engagement components are provided, and wherein the first guide surface and the second engagement components are configured such that when an axial external force is applied to the second transmission disk and the first guide surface is in contact with the second engagement components, the second engagement components are subject to unbalanced forces.

8. The transmission assembly of claim 4, wherein the second engagement component comprises a first guide portion, and wherein the first guide portion is configured to contact with the first guide surface to guide the second engagement component to slide along the first guide surface and to transmit a driving force when the second engagement component is in engagement with the first engagement component.

9. The transmission assembly of claim 1, wherein a first matching surface is formed on the end face where the second engagement component is situated, and the second engagement component is provided on the first matching surface, wherein the first matching surface is configured not to hinder the second engagement component from moving along the first guide surface and getting into engagement with the first engagement component.

10. The transmission assembly of claim 9, wherein the first matching surface is configured such that when the second engagement component is in engagement with the first engagement component, the first matching surface at least partially abuts against the first guide surface.

11. The transmission assembly of claim 9, wherein the first guide surface has at least one peak and at least one valley that are circumferentially distributed along the end face where the first guide surface is situated, and the first engagement component is provided at the valley of the first guide surface;

wherein the first matching surface has at least one peak and at least one valley that are circumferentially distributed along a corresponding end face, and the second engagement component is provided at the peak of the first matching surface;

wherein the peak of the first matching surface is configured in correspondence with the valley of the first guide surface, and the valley of the first matching surface is configured in correspondence with the peak of the first guide surface; and wherein the valley of the first matching surface is configured not to hinder an engagement between the first and second engagement components.

12. The transmission assembly of claim 11, wherein the valley of the first matching surface is configured such that when the first transmission disk is in engagement with the second transmission disk, the valley of the first matching surface is not in contact with a corresponding peak of the first guide surface at all, or the valley of the first matching surface is not in contact with a corresponding peak of the first guide surface, while a line contact or a surface contact is formed between two side portions of the valley of the first matching surface and two side portions of the corresponding peak of the first guide surface.

13. The transmission assembly of claim 9, wherein the first guide surface has at least one peak and at least one valley that are circumferentially distributed along the end face where the first guide surface is situated, and the first engagement component is provided at the valley of the first guide surface;

wherein the peak of the first matching surface is configured in correspondence with the valley of the first guide surface, and the valley of the first matching surface is configured in correspondence with the peak of the first guide surface; and the first matching surface is further provided with a first accommodating groove thereon, the accommodating groove configured for accommodating the peak of the first guide surface.

14. The transmission assembly of claim 1, further comprising a third transmission disk, wherein the first transmission disk, the second transmission disk and the third transmission disk are coupled in sequence;

wherein the second transmission disk further has a fourth end opposing the third end, and the third transmission disk has a fifth end arranged face to face with the fourth end;

wherein one of an end face of the fourth end and an end face of the fifth end has a second guide surface formed thereon, and the other one of the end face of the fourth end and the end face of the fifth end is provided with a fourth engagement component, wherein at least one third engagement component is provided on the second guide surface, and the fourth engagement component is configured to be engageable with the third engagement component, and wherein the fourth engagement component is configured to slide along the second guide surface until the fourth engagement component is engaged with the third engagement component to allow a torque transfer between the second transmission disk and the third transmission disk.

15. The transmission assembly of claim 14, wherein the first engagement component is shaped and sized identically to the third engagement component, wherein the second engagement component is shaped and sized identically to the fourth engagement component, and wherein the first guide surface is shaped identically to the second guide surface; and/or the fourth engagement component and the second engagement component are alternately arranged along a circumferential direction of the transmission assembly.

16. The transmission assembly of claim 14, wherein the transmission assembly comprises at least two second transmission disks that are mutually engaged, one of which is engaged with the first transmission disk, and another one of which is engaged with the third transmission disk.

17. A surgical instrument system for a surgical robot, comprising:

a driving force box comprising a first box body and a driving mechanism disposed in the first box body, the first box body provided thereon with at least one output hole;

at least one sterile plate, each provided with at least one transmission hole;

a surgical instrument comprising an instrument shaft, an instrument terminal and an instrument box, the instrument box comprising a second box body and a transmission module, wherein the transmission module is disposed in the second box body and configured to drive the instrument shaft and/or the instrument terminal to move, and the second box body is provided thereon with at least one input hole; and the transmission assembly of claim 1, wherein:

the driving force box, the sterile plate and the instrument box are arranged in sequence;

the first transmission disk is provided in the output hole and further comprises a first end opposite to the second end, the first end of the first transmission disk coupled to the driving mechanism; wherein the second transmission disk is provided in the transmission hole, and the third transmission disk is provided in the input hole and further comprises a sixth end opposite to the fifth end, the sixth end of the third transmission disk coupled to the transmission module; and when the first transmission disk, the second transmission disk and the third transmission disk are engaged in sequence, a driving force provided by the driving mechanism is transferred by the transmission assembly to the transmission module which in turn drives the instrument shaft and/or the instrument terminal to move.

18. The surgical instrument system of claim 17, further comprising:

at least one position correction magnet set, wherein the third transmission disk has a zero position, and the position correction magnet set is configured to help the third transmission disk reach the zero position;

and/or at least one anti-dislocation magnet set, wherein the transmission assembly has a worst position and the anti-dislocation magnet set is configured to prevent the transmission assembly from reaching the worst position.

19. The surgical instrument system of claim 18, wherein the position correction magnet set comprises a first magnet and a second magnet, the first magnet disposed on the third transmission disk, the second magnet disposed on the instrument box, the first and second magnets configured to attract each other to help the third transmission disk reach the zero position.

20. The surgical instrument system of claim 18, wherein the anti-dislocation magnet set comprises a third magnet and a fourth magnet, the third magnet provided on the second transmission disk, the fourth magnet provided on the sterile plate, and wherein the third and the fourth magnets are arranged to repel each other so as to keep the transmission assembly off the worst position under an action of a repulsive force.

21. The surgical instrument system of claim 17, further comprising: a circumferential limiter configured to limit a range of rotation of the third transmission disk, and/or an axial limiter configured to prevent the second transmission disk from dislodging from the sterile plate.

22. The surgical instrument system of claim 21, wherein the circumferential limiter comprises a limiting protrusion provided on a circumferential side wall of the third transmission disk and a slide groove provided in an inner wall of the input hole, and wherein the limiting protrusion is provided within the slide groove and is moveable along the slide groove.

23. The surgical instrument system of claim 21, wherein the sterile plate comprises a sterile substrate and a sterile cover, the sterile substrate coupled to the driving force box, the sterile substrate provided thereon with a first through hole, the sterile cover provided thereon with a second through hole, the second through hole constituting the transmission hole together with the first through hole, wherein the axial limiter comprises a limiting collar provided on a circumferential side wall of the second transmission disk, and wherein a section of the second through hole close to the first through hole has an inner diameter greater than each of an inner diameter of a section of the second through hole away from the first through hole and an inner diameter of the first through hole, and matches an outer diameter of the limiting collar.

24. A transmission assembly for a surgical instrument, comprising a first transmission disk and a second transmission disk, wherein:

the first transmission disk has a second end, and the second transmission disk has a third end arranged face to face with the second end, one of an end face of the second end and an end face of the third end has a first guide surface formed thereon, and the other one of the end face of the second end and the end face of the third end is provided with a second engagement component, wherein at least one first engagement component is provided on the first guide surface, and the second engagement component is configured to be engageable with the first engagement component, and the second engagement component is configured to move along the first guide surface until the second engagement component is engaged with the first engagement component to allow a torque transfer between the first transmission disk and the second transmission disk, wherein each of the second engagement components comprises a first guide portion, each first guide portion comprising two wedge surfaces and one first transition surface between the two wedge surfaces, wherein the first transition surface is cut by a first group of flat or curved imaginary cutting surfaces and a first group of cut intersection lines are formed between the first transition surface and the first group of flat or curved imaginary cutting surfaces, and wherein a first intersection line is defined as a connecting line formed by connecting each of feature points of the first group of cut intersection lines;

wherein the first guide surface comprises a plurality of guide sub-surfaces, adjacent guide sub-surfaces being connected by a second transition surface at the peak of the first guide surface, wherein the second transition surface is cut by a second group of flat or curved imaginary cutting surfaces and a second group of cut intersection lines are formed between the second transition surface and the second group of flat or curved imaginary cutting surfaces, and wherein a second intersection line is defined as a connecting line formed by connecting each of feature points of the second group of cut intersection lines; and wherein the first and second intersection lines are configured such that when the first engagement component is in engagement with the second engagement components, an axial projection of a first intersection line at least partially coincides with an axial projection of a corresponding second intersection line; or a plurality of the first intersection lines and a plurality of the second intersection lines are configured such that when the first engagement component is in engagement with the second engagement components, at least two of axial projections of the plurality of the first intersection lines are collinear and at least two of axial projections of the plurality of the second intersection lines are collinear.

* * * * *